US006762295B2

(12) United States Patent
Doidge et al.

(10) Patent No.: US 6,762,295 B2
(45) Date of Patent: Jul. 13, 2004

(54) PROTECTIVE HELICOBACTER ANTIGENS

(75) Inventors: Christopher Vincent Doidge, Box Hill (AU); Adrian Lee, Lane Cove (AU); Fiona Jane Radcliff, Sydney (AU); Dianna Margaret Hocking, Flemington (AU); Elizabeth Ann Webb, Eltham (AU)

(73) Assignees: CSL Limited, Parkville (AU); The University of New South Wales, Kensington (AU)

( * ) Notice: Subject to any disclaimer, the term of this patent is extended or adjusted under 35 U.S.C. 154(b) by 32 days.

(21) Appl. No.: 08/945,038

(22) PCT Filed: Apr. 19, 1996

(86) PCT No.: PCT/AU96/00225

§ 371 (c)(1),
(2), (4) Date: Dec. 23, 1997

(87) PCT Pub. No.: WO96/33220

PCT Pub. Date: Oct. 24, 1996

(65) Prior Publication Data

US 2002/0146423 A1 Oct. 10, 2002

(30) Foreign Application Priority Data

Apr. 21, 1995 (AU) ............................................. PN2575
Jul. 3, 1995 (AU) ............................................. PN3931
Jan. 16, 1996 (AU) ............................................. PN7565

(51) Int. Cl.[7] ............................................. C07H 21/04
(52) U.S. Cl. ..................... 536/23.7; 536/23.1; 514/44; 435/6; 435/69.1; 435/172.2; 435/172.3; 435/252.33; 435/320.1
(58) Field of Search ........................... 424/184.1; 435/6, 435/69.1, 172.2, 172.3, 252.1, 252.33, 320.1; 514/44; 536/23.1, 23.7

(56) References Cited

U.S. PATENT DOCUMENTS 5,262,156 A   11/1993  Alemohammad ............ 424/92
5,527,678 A *  6/1996  Blaser et al. .................. 435/6

FOREIGN PATENT DOCUMENTS

| WO | WO 93/07273 | 4/1993 |
| WO | 9405771 A * | 3/1994 |
| WO | WO 95/03824 | 2/1995 |
| WO | WO 95/22563 | 8/1995 |
| WO | WO 96/01272 | 1/1996 |

OTHER PUBLICATIONS

Hillier, L. et al, Genebank Acc. # W32290, The WashU–Merck Est Project, Available to Public in, 1995.*
Venter, J.C. et al, Jan. 21, 1992, D. *Melanogaster octopamine* receptor coding sequence, Genbank Accu No. Q21928, 1992.*
Collins, D.M. , Genebank Acc. No. Q62621, Apr. 27, 1994.*
Markovics, A. et al, Genebank Acc No. Q 45940, Aug. 4, 1993.*
Ying, H et al, J. Immunol., vol. 154(6), p2743–2752, 1995.*
Taylor, D.E. et al, J. of Bacteriol. , Nov. 1992, vol. 174 No./21, p 6800–6806.*
Bukanov, N.O. et al, Molecular Microbiol. , Feb. 1994, vol. 11(3), p509–523.*
Blanchard, TG et al, Gut (37 Suppl 1, A31), Jul., 1995, (abstract).*
Jihau J. et al, Chinese J. Microbiol. & Immunol, Beijing, 1995, vol. 15(2), p95–98 (abstract).*
Orkin, S. H. et al, Dec. 1995, Report and Recommendations of the Panel to Assess the NIH Investment in Research on Gene Therapy.*
Ho, B. et al, Eur. J. Gasteroenterol & Hepatol. , vol7(2), Feb., p121–124, 1995.*
Chen, M et al.Gastroenterology, Vo . . . 104(4), Apr. p. 681, col. 1, second abstract, 1993.*
Heap et al, Microb. Ecol. Health Dis., vol. 4, p. S119, abstract H2–4, Oct. 7–10, 1991.*
Dunkley, M.L. et al, Microb. Ecol. Health Dis, vol. 4(special issue), p. S148, abstract H5–3, Oct. 7–10, 1991.*
Tummuru et al, Molecular Microbiology, vol. 18(5), pp. 867–876, 1995.*
Thompson, S.A. et al, Infection and Immunity, vol. 63(6), pp. 2185–2193, Jun. 1995.*
Huang, J et al, Infection and Immunity, vol. 63(5), pp. 1732–1738, May, 1995.*
Thomas, W.D. et al, ACTA Gastro–Enterologica Belgica, Sep. 21–25, 1993, vol. 56, p. 5, 1993.*
Hughes, NJ et al, J. Bacteriology, vol. 177(14), pp. 3953–3959, Jul., 1995.*
Moll, G et al, Eur. J. Biochem., vol. 234, p. 947–952, 1995.*
Dore'–Davin, C. et al, Gastroenterology, vol. 110(4), Apr. 1996, p. A898, abstract, col. 1, 1996.*
Narahara et al, Gene, vol. 122(1), pp. 181–185, 1992, Accession No. X62374, sequence alignment.*
Markovics, et al, EP554064, publication date Aug. 1993, accession No. Q45940, sequence alignment.*
M. Kostrzynska et al., Molecular Characterization of a conserved 20–Kilodalton Membrane–Associated Lipoprotein Antigen of *Helicobacter Pylori*, J. Bacteriol. vol. 176, No. 19., 10/94, pp. 5938–5948.

(List continued on next page.)

*Primary Examiner*—Lynette R. F. Smith
*Assistant Examiner*—Ginny Allen Portner
(74) *Attorney, Agent, or Firm*—Foley & Lardner

(57) ABSTRACT

Protective Helicobacter antigens, especially H. pylori antigens, and the use of these antigens for the treatment of or prevention of, gastroduodenal disease associated with H. pylori infection.

11 Claims, 2 Drawing Sheets

OTHER PUBLICATIONS

J. Faulde et al., Humoral immune response against *Helicobacter pylori* as determined by immunoblot, Electrophoresis 1993, pp. 945–951.

P. Doig et al., Identification of Surface–Exposed Outer Membrane Antigens of *Helicobacter pylori* Infect. Immun. vol. 62, No. 10, 10/94, pp. 4526–4533.

E.B. Drouet et al., Characterization of an Immunoreactive Species–Specific 19–Kilodalton Outer Membrane Protein from *Helicobacter pylori*, J. Clin. Microbiol. vol. 29, No. 8, 8/91, pp. 1620–1624.

C.J. Luke et al., Identification of a 29 kDa flagellar sheath protein in *Helicobacter pylori* using a murine monoclonal antibody, Microbiology (1995), pp. 597–604.

* cited by examiner

A. Molecular mass (kDa)

B. Molecular mass (kDa)

A.

B.

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 378 base pairs
      (B) TYPE: nucleic acid
      (C) STRANDEDNESS: single -continued (D) TOPOLOGY: linear (ii) MOLECULE TYPE: cDNA (vi) ORIGINAL SOURCE:
        (A) ORGANISM: Helicobacter pylori (vii) IMMEDIATE SOURCE:
        (B) CLONE: Clone C.3.5

(ix) FEATURE:
        (A) NAME/KEY: CDS
        (B) LOCATION: 1..375

(xi) SEQUENCE DESCRIPTION: SEQ ID NO:1:

```
ATG GCA ATT TCA AAA GAA GAA GTG TTA GAG TAT ATT GGT TCA TTG AGC      48
Met Ala Ile Ser Lys Glu Glu Val Leu Glu Tyr Ile Gly Ser Leu Ser
 1               5                  10                  15

GTT TTA GAG CTT TCT GAA TTG GTT AAA ATG TTT GAG GAA AAA TTT GGC      96
Val Leu Glu Leu Ser Glu Leu Val Lys Met Phe Glu Glu Lys Phe Gly
             20                  25                  30

GTG AGC GCG ACT CCA ACG GTC GTA GCG GGT GCG GCT GTA GCT GGC GGT     144
Val Ser Ala Thr Pro Thr Val Val Ala Gly Ala Ala Val Ala Gly Gly
         35                  40                  45

GCA GCG GCT GAG AGC GAA GAA AAA ACC GAA TTT AAT GTG ATT TTG GCC     192
Ala Ala Ala Glu Ser Glu Glu Lys Thr Glu Phe Asn Val Ile Leu Ala
 50                  55                  60

GAT AGC GGT GCT GAA AAA ATT AAG GTG ATT AAA GTG GTT CGT GAA ATC     240
Asp Ser Gly Ala Glu Lys Ile Lys Val Ile Lys Val Val Arg Glu Ile
 65                  70                  75                  80

ACT GGA CTT GGC CTG AAA GAA GCT AAA GAC GCT ACC GAA AAA ACC CCT     288
Thr Gly Leu Gly Leu Lys Glu Ala Lys Asp Ala Thr Glu Lys Thr Pro
             85                  90                  95

CAT GTG CTT AAA GAG GGC GTG AAT AAA GAA GAA GCT GAA ACC ATC AAG     336
His Val Leu Lys Glu Gly Val Asn Lys Glu Glu Ala Glu Thr Ile Lys
        100                 105                 110

AAG AAA CTT GAA GAA GTA GGC GCT AAG GTT GAA GTC AAG TAA             378
Lys Lys Leu Glu Glu Val Gly Ala Lys Val Glu Val Lys
        115                 120                 125
```

(2) INFORMATION FOR SEQ ID NO:2:

(i) SEQUENCE CHARACTERISTICS:
        (A) LENGTH: 125 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ile Ser Lys Glu Glu Val Leu Glu Tyr Ile Gly Ser Leu Ser
 1               5                  10                  15

Val Leu Glu Leu Ser Glu Leu Val Lys Met Phe Glu Glu Lys Phe Gly
             20                  25                  30

Val Ser Ala Thr Pro Thr Val Val Ala Gly Ala Ala Val Ala Gly Gly
         35                  40                  45

Ala Ala Ala Glu Ser Glu Glu Lys Thr Glu Phe Asn Val Ile Leu Ala
 50                  55                  60

Asp Ser Gly Ala Glu Lys Ile Lys Val Ile Lys Val Val Arg Glu Ile
 65                  70                  75                  80

Thr Gly Leu Gly Leu Lys Glu Ala Lys Asp Ala Thr Glu Lys Thr Pro
             85                  90                  95

His Val Leu Lys Glu Gly Val Asn Lys Glu Glu Ala Glu Thr Ile Lys
```

```
                         100                 105                 110
Lys Lys Leu Glu Glu Val Gly Ala Lys Val Glu Val Lys
         115                 120                 125

(2) INFORMATION FOR SEQ ID NO:3:

(i) SEQUENCE CHARACTERISTICS:
        (A) LENGTH: 990 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: helicobacter pylori (vii) IMMEDIATE SOURCE:
        (B) CLONE: clone E2.5

(ix) FEATURE:
        (A) NAME/KEY: CDS
        (B) LOCATION: 1..987

(xi) SEQUENCE DESCRIPTION: SEQ ID NO:3:

ATG TCA AAT AGC ATG TTG GAT AAA AAT AAA GCG ATT CTT ACA GGG GGT         48
Met Ser Asn Ser Met Leu Asp Lys Asn Lys Ala Ile Leu Thr Gly Gly
 1               5                  10                  15

GGG GCT TTA TTG TTA GGG CTA ATC GTG CTT TTT TAT TTG GCT TAT CGC         96
Gly Ala Leu Leu Leu Gly Leu Ile Val Leu Phe Tyr Leu Ala Tyr Arg
                 20                  25                  30

CCT AAG GCT GAA GTG TTG CAA GGA TTT TTG GAA GCC AGA GAA TAC AGC        144
Pro Lys Ala Glu Val Leu Gln Gly Phe Leu Glu Ala Arg Glu Tyr Ser
             35                  40                  45

GTG AGT TCC AAA GTC CCT GGC CGC ATT GAA AAG GTG TTT GTT AAA AAA        192
Val Ser Ser Lys Val Pro Gly Arg Ile Glu Lys Val Phe Val Lys Lys
         50                  55                  60

GGC GAT CGC ATT AAA AAG GGC GAT TTG GTT TTT AGC ATT TCT AGC CCT        240
Gly Asp Arg Ile Lys Lys Gly Asp Leu Val Phe Ser Ile Ser Ser Pro
 65                  70                  75                  80

GAA TTA GAA GCC AAG CTC GCT CAA GCT GAA GCC GGG CAT AAA GCC GCT        288
Glu Leu Glu Ala Lys Leu Ala Gln Ala Glu Ala Gly His Lys Ala Ala
                 85                  90                  95

AAA GCG CTT AGC GAT GAA GTC AAA AGA GGC TCA AGA GAC GAA ACG ATC        336
Lys Ala Leu Ser Asp Glu Val Lys Arg Gly Ser Arg Asp Glu Thr Ile
            100                 105                 110

AAT TCT GCA AGA GAC GTT TGG CAA GCG GCC AAA TCT CAA GCC ACT TTA        384
Asn Ser Ala Arg Asp Val Trp Gln Ala Ala Lys Ser Gln Ala Thr Leu
        115                 120                 125

GCC AAA GAG ACT TAT AAG CGC GTT CAA GAT TTG TAT GAT AAT GGC GTG        432
Ala Lys Glu Thr Tyr Lys Arg Val Gln Asp Leu Tyr Asp Asn Gly Val
130                 135                 140

GCG AGC TTG CAA AAG CGC GAT GAA GCC TAT GCG GCT TAT GAA AGC ACT        480
Ala Ser Leu Gln Lys Arg Asp Glu Ala Tyr Ala Ala Tyr Glu Ser Thr
145                 150                 155                 160

AAA TAC AAC GAG AGC GCG GCT TAC CAA AAG TAT AAA ATG GCT TTA GGG        528
Lys Tyr Asn Glu Ser Ala Ala Tyr Gln Lys Tyr Lys Met Ala Leu Gly
                165                 170                 175

GGG GCG AGC TCT GAA AGT AAG ATT GCC GCT AAG GCT AAA GAG AGC GCG        576
Gly Ala Ser Ser Glu Ser Lys Ile Ala Ala Lys Ala Lys Glu Ser Ala
            180                 185                 190

GCT TTA GGG CAA GTG AAT GAA GTG GAG TCT TAT TTA AAA GAT GTC AAA        624
Ala Leu Gly Gln Val Asn Glu Val Glu Ser Tyr Leu Lys Asp Val Lys
        195                 200                 205
```

```
GCG ACA GCC CCA ATT GAT GGG GAA GTG AGT AAT GTG CTT TTA AGC GGT      672
Ala Thr Ala Pro Ile Asp Gly Glu Val Ser Asn Val Leu Leu Ser Gly
210                 215                 220

GGC GAG CTT AGC CCT AAG GGC TTT CCT GTG GTG CTC ATG ATT GAT TTA      720
Gly Glu Leu Ser Pro Lys Gly Phe Pro Val Val Leu Met Ile Asp Leu
225                 230                 235                 240

AAG GAT AGT TGG TTA AAA ATC AGC GTG CCT GAA AAG TAT TTG AAC GAT      768
Lys Asp Ser Trp Leu Lys Ile Ser Val Pro Glu Lys Tyr Leu Asn Asp
                245                 250                 255

TTT AAA GTG GGT AAG GAA TTT GAA GGT TAT ATC CCG GCG TTG AAA AGA      816
Phe Lys Val Gly Lys Glu Phe Glu Gly Tyr Ile Pro Ala Leu Lys Arg
                260                 265                 270

AGC GCG AAA TTC AGG GTC AAA TAT TTG AGC GTG ATG GGG GAT TTT GCG      864
Ser Ala Lys Phe Arg Val Lys Tyr Leu Ser Val Met Gly Asp Phe Ala
                275                 280                 285

ACT TGG AAA GCG ACG AAT AAT TCC AAC ACT TAC GAC ATG AAA AGC TAT      912
Thr Trp Lys Ala Thr Asn Asn Ser Asn Thr Tyr Asp Met Lys Ser Tyr
290                 295                 300

GAA GTG GAG GCC ATA CCC TTA GAA GAG TTG GAA AAT TTT AGG GTA GGG      960
Glu Val Glu Ala Ile Pro Leu Glu Glu Leu Glu Asn Phe Arg Val Gly
305                 310                 315                 320

ATG AGC GTG TTA GTT ACC ATT AAA CCT TAA                              990
Met Ser Val Leu Val Thr Ile Lys Pro
                325

(2) INFORMATION FOR SEQ ID NO:4:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO:4:

Met Ser Asn Ser Met Leu Asp Lys Asn Lys Ala Ile Leu Thr Gly Gly
  1               5                  10                  15

Gly Ala Leu Leu Leu Gly Leu Ile Val Leu Phe Tyr Leu Ala Tyr Arg
                 20                  25                  30

Pro Lys Ala Glu Val Leu Gln Gly Phe Leu Glu Ala Arg Glu Tyr Ser
            35                  40                  45

Val Ser Ser Lys Val Pro Gly Arg Ile Glu Lys Val Phe Val Lys Lys
 50                  55                  60

Gly Asp Arg Ile Lys Lys Gly Asp Leu Val Phe Ser Ile Ser Ser Pro
 65                  70                  75                  80

Glu Leu Glu Ala Lys Leu Ala Gln Ala Glu Ala Gly His Lys Ala Ala
                 85                  90                  95

Lys Ala Leu Ser Asp Glu Val Lys Arg Gly Ser Arg Asp Glu Thr Ile
            100                 105                 110

Asn Ser Ala Arg Asp Val Trp Gln Ala Ala Lys Ser Gln Ala Thr Leu
            115                 120                 125

Ala Lys Glu Thr Tyr Lys Arg Val Gln Asp Leu Tyr Asp Asn Gly Val
            130                 135                 140

Ala Ser Leu Gln Lys Arg Asp Glu Ala Tyr Ala Ala Tyr Glu Ser Thr
145                 150                 155                 160

Lys Tyr Asn Glu Ser Ala Ala Tyr Gln Lys Tyr Lys Met Ala Leu Gly
                165                 170                 175

Gly Ala Ser Ser Glu Ser Lys Ile Ala Ala Lys Ala Lys Glu Ser Ala
```

```
                    180                 185                 190
Ala Leu Gly Gln Val Asn Glu Val Glu Ser Tyr Leu Lys Asp Val Lys
            195                 200                 205

Ala Thr Ala Pro Ile Asp Gly Glu Val Ser Asn Val Leu Leu Ser Gly
    210                 215                 220

Gly Glu Leu Ser Pro Lys Gly Phe Pro Val Val Leu Met Ile Asp Leu
225                 230                 235                 240

Lys Asp Ser Trp Leu Lys Ile Ser Val Pro Glu Lys Tyr Leu Asn Asp
                245                 250                 255

Phe Lys Val Gly Lys Glu Phe Glu Gly Tyr Ile Pro Ala Leu Lys Arg
            260                 265                 270

Ser Ala Lys Phe Arg Val Lys Tyr Leu Ser Val Met Gly Asp Phe Ala
    275                 280                 285

Thr Trp Lys Ala Thr Asn Asn Ser Asn Thr Tyr Asp Met Lys Ser Tyr
290                 295                 300

Glu Val Glu Ala Ile Pro Leu Glu Glu Leu Asn Phe Arg Val Gly
305                 310                 315                 320

Met Ser Val Leu Val Thr Ile Lys Pro
                325

(2) INFORMATION FOR SEQ ID NO:5:

(i) SEQUENCE CHARACTERISTICS:
        (A) LENGTH: 1302 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Helicobacter pylori (vii) IMMEDIATE SOURCE:
        (B) CLONE: Clone G3.8

(ix) FEATURE:
        (A) NAME/KEY: CDS
        (B) LOCATION: 1..1299

(xi) SEQUENCE DESCRIPTION: SEQ ID NO:5:

ATG TTT GGG AAT AAG CAG TTG CAA CTT CAA ATC AGT CAG AAA GAT TCT      48
Met Phe Gly Asn Lys Gln Leu Gln Leu Gln Ile Ser Gln Lys Asp Ser
 1               5                  10                  15

GAG ATT GCG GAG TTA AAA AAG GAA GTC AAT CTC TAT CAA AGC CTT TTA      96
Glu Ile Ala Glu Leu Lys Lys Glu Val Asn Leu Tyr Gln Ser Leu Leu
             20                  25                  30

AAT TTG TGC TTG CAT GAA GGT TTT GTA GGT ATT AAA AAC AAT AAA GTC     144
Asn Leu Cys Leu His Glu Gly Phe Val Gly Ile Lys Asn Asn Lys Val
         35                  40                  45

GTT TTT AAA AGT GGG AAT CTT GCA AGC TTA AAC AAT TTA GAA GAA CAA     192
Val Phe Lys Ser Gly Asn Leu Ala Ser Leu Asn Asn Leu Glu Glu Gln
     50                  55                  60

AGC GTT CAT TTT AAA GAA AAT GCA GAG AGC GTT GAT TTG CAA GGG GTT     240
Ser Val His Phe Lys Glu Asn Ala Glu Ser Val Asp Leu Gln Gly Val
 65                  70                  75                  80

TCT TAT TCT TTA AAA AGC CAA AAT ATT GAC GGC GTG CAG TAT TTT TCA     288
Ser Tyr Ser Leu Lys Ser Gln Asn Ile Asp Gly Val Gln Tyr Phe Ser
                 85                  90                  95

TTG GCT AAA AAA ACA GGT TGT GTG GGG GAA TAC CAT AAA AAT GAT TTG     336
Leu Ala Lys Lys Thr Gly Cys Val Gly Glu Tyr His Lys Asn Asp Leu
            100                 105                 110
```

-continued

| | |
|---|---|
| TTT AAG ACT TTT TGC GCG AGC TTA AAA GAA GGC TTA GAG AAC GCA CAA<br>Phe Lys Thr Phe Cys Ala Ser Leu Lys Glu Gly Leu Glu Asn Ala Gln<br>           115                    120                    125 | 384 |
| GAA AGC ATG CAG TAT TTC CAT CAA GAA ACC GGC TTG CTC TTG AAT GCG<br>Glu Ser Met Gln Tyr Phe His Gln Glu Thr Gly Leu Leu Leu Asn Ala<br>130                    135                    140 | 432 |
| GCT AAA AAT GGC GAA GCG CAT TCT ACT GAA GGA TTA GGG ACC GTT AAT<br>Ala Lys Asn Gly Glu Ala His Ser Thr Glu Gly Leu Gly Thr Val Asn<br>145                    150                    155                    160 | 480 |
| AAA ACG GGT CAA GAC ATT GAA TCG CTT TAT GAA AAG ATG CAA AAC GCC<br>Lys Thr Gly Gln Asp Ile Glu Ser Leu Tyr Glu Lys Met Gln Asn Ala<br>           165                    170                    175 | 528 |
| ACT TCG TTA GCG GAC TCC CTC AAC CAA CGG AGC AAT GAA ATC ACT CAA<br>Thr Ser Leu Ala Asp Ser Leu Asn Gln Arg Ser Asn Glu Ile Thr Gln<br>           180                    185                    190 | 576 |
| GTC ATT TCT TTG ATT GAT GAT ATT GCA GAA CAA ACC AAT CTC TTA GCC<br>Val Ile Ser Leu Ile Asp Asp Ile Ala Glu Gln Thr Asn Leu Leu Ala<br>           195                    200                    205 | 624 |
| CTA AAT GCC GCT ATT GAG GCC GCA CGA GCG GGC GAG CAT GGG AGA GGG<br>Leu Asn Ala Ala Ile Glu Ala Ala Arg Ala Gly Glu His Gly Arg Gly<br>210                    215                    220 | 672 |
| TTT GCG GTG GTG GCT GAT GAG GTG AGA AAA CTC GCT GAA AAA ACC CAA<br>Phe Ala Val Val Ala Asp Glu Val Arg Lys Leu Ala Glu Lys Thr Gln<br>225                    230                    235                    240 | 720 |
| AAA GCC ACT AAA GAA ATC GTT GTC GTG GTT AAA AGC ATG CAA CAA GAA<br>Lys Ala Thr Lys Glu Ile Val Val Val Val Lys Ser Met Gln Gln Glu<br>           245                    250                    255 | 768 |
| GCC AAC GAT ATT CAA ACC AAC ACC CAT GAC ATT AAT TCT ATT GTA AGC<br>Ala Asn Asp Ile Gln Thr Asn Thr His Asp Ile Asn Ser Ile Val Ser<br>           260                    265                    270 | 816 |
| TCT ATT AAG GGC GAT GTG GAA GAG CTT AAA TCC ACC GTG AAA AAT AAC<br>Ser Ile Lys Gly Asp Val Glu Glu Leu Lys Ser Thr Val Lys Asn Asn<br>           275                    280                    285 | 864 |
| ATG ATT GTC GCG CAA GCG GCA AAA TAC ACC ATC TAC AAT ATC AAT AAC<br>Met Ile Val Ala Gln Ala Ala Lys Tyr Thr Ile Tyr Asn Ile Asn Asn<br>290                    295                    300 | 912 |
| CGG GTG TTT TGC GGT CTG GCT AAA TTG GAT CAT GTG GTC TTT AAA AAC<br>Arg Val Phe Cys Gly Leu Ala Lys Leu Asp His Val Val Phe Lys Asn<br>305                    310                    315                    320 | 960 |
| AAT CTT TAT GGC ATG GTT TTT GGT CTC AAC TCC TTT GAT ATT ACC AGC<br>Asn Leu Tyr Gly Met Val Phe Gly Leu Asn Ser Phe Asp Ile Thr Ser<br>           325                    330                    335 | 1008 |
| CAT AAG AGT TGC CGT TTA GGC AAA TGG TAT TAT GAG GGT GCG GGC AAA<br>His Lys Ser Cys Arg Leu Gly Lys Trp Tyr Tyr Glu Gly Ala Gly Lys<br>           340                    345                    350 | 1056 |
| GAG AAT TTT TCC AAC ACT TCA GGC TAT AGA GCT TTA GAA AGC CAC CAT<br>Glu Asn Phe Ser Asn Thr Ser Gly Tyr Arg Ala Leu Glu Ser His His<br>           355                    360                    365 | 1104 |
| GCG AGC GTG CAT GCT GAA GCT AAT GAT TTG GTT AAA GCC GTT CAA GAA<br>Ala Ser Val His Ala Glu Ala Asn Asp Leu Val Lys Ala Val Gln Glu<br>370                    375                    380 | 1152 |
| GAT CAC ATT ACC GAT TCA AAA TAC CTA GAG CAT AAA GTG CAT TTA ATG<br>Asp His Ile Thr Asp Ser Lys Tyr Leu Glu His Lys Val His Leu Met<br>385                    390                    395                    400 | 1200 |
| GAA GAT AGC GCT AAA CAT GTC AAA GAA AAT ATT GAT AAG ATG TTT TAC<br>Glu Asp Ser Ala Lys His Val Lys Glu Asn Ile Asp Lys Met Phe Tyr<br>           405                    410                    415 | 1248 |
| GAA AAA CAA GAC GAG CTC AAT AAA ATC ATT GAA AAA ATT CAA AAA GGC<br>Glu Lys Gln Asp Glu Leu Asn Lys Ile Ile Glu Lys Ile Gln Lys Gly | 1296 |

-continued

```
            420             425             430
GAA TGA                                                                        1302
Glu (2) INFORMATION FOR SEQ ID NO:6:

(i) SEQUENCE CHARACTERISTICS:
        (A) LENGTH: 433 amino acids
        (B) TYPE: amino acid
        (D) TOPOLOGY: linear (ii) MOLECULE TYPE: protein (xi) SEQUENCE DESCRIPTION: SEQ ID NO:6:

Met Phe Gly Asn Lys Gln Leu Gln Leu Gln Ile Ser Gln Lys Asp Ser
 1               5                  10                  15

Glu Ile Ala Glu Leu Lys Lys Glu Val Asn Leu Tyr Gln Ser Leu Leu
            20                  25                  30

Asn Leu Cys Leu His Glu Gly Phe Val Gly Ile Lys Asn Asn Lys Val
        35                  40                  45

Val Phe Lys Ser Gly Asn Leu Ala Ser Leu Asn Asn Leu Glu Glu Gln
    50                  55                  60

Ser Val His Phe Lys Glu Asn Ala Glu Ser Val Asp Leu Gln Gly Val
65                  70                  75                  80

Ser Tyr Ser Leu Lys Ser Gln Asn Ile Asp Gly Val Gln Tyr Phe Ser
                85                  90                  95

Leu Ala Lys Lys Thr Gly Cys Val Gly Glu Tyr His Lys Asn Asp Leu
            100                 105                 110

Phe Lys Thr Phe Cys Ala Ser Leu Lys Glu Gly Leu Glu Asn Ala Gln
        115                 120                 125

Glu Ser Met Gln Tyr Phe His Gln Glu Thr Gly Leu Leu Leu Asn Ala
    130                 135                 140

Ala Lys Asn Gly Glu Ala His Ser Thr Glu Gly Leu Gly Thr Val Asn
145                 150                 155                 160

Lys Thr Gly Gln Asp Ile Glu Ser Leu Tyr Glu Lys Met Gln Asn Ala
                165                 170                 175

Thr Ser Leu Ala Asp Ser Leu Asn Gln Arg Ser Asn Glu Ile Thr Gln
            180                 185                 190

Val Ile Ser Leu Ile Asp Asp Ile Ala Glu Gln Thr Asn Leu Leu Ala
        195                 200                 205

Leu Asn Ala Ala Ile Glu Ala Ala Arg Ala Gly Glu His Gly Arg Gly
    210                 215                 220

Phe Ala Val Val Ala Asp Glu Val Arg Lys Leu Ala Glu Lys Thr Gln
225                 230                 235                 240

Lys Ala Thr Lys Glu Ile Val Val Val Lys Ser Met Gln Gln Glu
                245                 250                 255

Ala Asn Asp Ile Gln Thr Asn Thr His Asp Ile Asn Ser Ile Val Ser
            260                 265                 270

Ser Ile Lys Gly Asp Val Glu Glu Leu Lys Ser Thr Val Lys Asn Asn
        275                 280                 285

Met Ile Val Ala Gln Ala Ala Lys Tyr Thr Ile Tyr Asn Ile Asn Asn
    290                 295                 300

Arg Val Phe Cys Gly Leu Ala Lys Leu Asp His Val Val Phe Lys Asn
305                 310                 315                 320

Asn Leu Tyr Gly Met Val Phe Gly Leu Asn Ser Phe Asp Ile Thr Ser
                325                 330                 335
```

-continued

```
His Lys Ser Cys Arg Leu Gly Lys Trp Tyr Tyr Glu Gly Ala Gly Lys
            340                 345                 350

Glu Asn Phe Ser Asn Thr Ser Gly Tyr Arg Ala Leu Glu Ser His His
            355                 360                 365

Ala Ser Val His Ala Glu Ala Asn Asp Leu Val Lys Ala Val Gln Glu
            370                 375                 380

Asp His Ile Thr Asp Ser Lys Tyr Leu Glu His Lys Val His Leu Met
385                 390                 395                 400

Glu Asp Ser Ala Lys His Val Lys Glu Asn Ile Asp Lys Met Phe Tyr
            405                 410                 415

Glu Lys Gln Asp Glu Leu Asn Lys Ile Ile Glu Lys Ile Gln Lys Gly
            420                 425                 430

Glu
```

(2) INFORMATION FOR SEQ ID NO:7:

(i) SEQUENCE CHARACTERISTICS:
        (A) LENGTH: 771 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Helicobacter pylori (vii) IMMEDIATE SOURCE:
        (A) LIBRARY: Clone H5.1

(ix) FEATURE:
        (A) NAME/KEY: CDS
        (B) LOCATION: 1..768

(xi) SEQUENCE DESCRIPTION: SEQ ID NO:7:

```
ATG GGA TAC GCA AGC AAA TTA GCC TTG AAG ATT TGT TTG GCA AGT TTA      48
Met Gly Tyr Ala Ser Lys Leu Ala Leu Lys Ile Cys Leu Ala Ser Leu
1               5                   10                  15

TGT TTA TTT AGC GCT CTT GGT GCA GAA CAC CTT GAA CAA AAA AGG AAT      96
Cys Leu Phe Ser Ala Leu Gly Ala Glu His Leu Glu Gln Lys Arg Asn
                20                  25                  30

TAT ATT TAT AAA GGG GAG GAA GCC TAT AAT AAT AAG GAA TAT GAG CGG     144
Tyr Ile Tyr Lys Gly Glu Glu Ala Tyr Asn Asn Lys Glu Tyr Glu Arg
            35                  40                  45

GCG GCT TCT TTT TAT AAG AGC GCT ATT AAA AAT GGC GAG CCG CTT GCT     192
Ala Ala Ser Phe Tyr Lys Ser Ala Ile Lys Asn Gly Glu Pro Leu Ala
50                  55                  60

TAT GTT CTT TTA GGG ATC ATG TAT GAA AAT GGT AGG GGT GTG CCT AAA     240
Tyr Val Leu Leu Gly Ile Met Tyr Glu Asn Gly Arg Gly Val Pro Lys
65                  70                  75                  80

GAT TAC AAG AAA GCG GCT GAA TAT TTT CAA AAA GCG GTT GAT AAC GAT     288
Asp Tyr Lys Lys Ala Ala Glu Tyr Phe Gln Lys Ala Val Asp Asn Asp
                85                  90                  95

ATA CCT AGA GGG TAT AAC AAT TTA GGT GTG ATG TAT AAA GAG GGT AGG     336
Ile Pro Arg Gly Tyr Asn Asn Leu Gly Val Met Tyr Lys Glu Gly Arg
            100                 105                 110

GGC GTT CCT AAA GAT GAA AAG AAA GCC GTG GAG TAT TTT AGA ATA GCT     384
Gly Val Pro Lys Asp Glu Lys Lys Ala Val Glu Tyr Phe Arg Ile Ala
            115                 120                 125

ACA GAG AAG GGC TAT GCT AAC GCT TAT ATC AAC TTA GGC ATC ATG TAT     432
Thr Glu Lys Gly Tyr Ala Asn Ala Tyr Ile Asn Leu Gly Ile Met Tyr
130                 135                 140
```

-continued

```
ATG GAG GGT AGG GGA GTT CCA AGC AAC TAT GTG AAA GCG ACA GAG TGC    480
Met Glu Gly Arg Gly Val Pro Ser Asn Tyr Val Lys Ala Thr Glu Cys
145                 150                 155                 160

TTT AGA AAA GCG ATG CAT AAG GGT AAT GTA GAA GCT TAT ATC CTT TTA    528
Phe Arg Lys Ala Met His Lys Gly Asn Val Glu Ala Tyr Ile Leu Leu
                165                 170                 175

GGG GAT ATT TAT TAT AGC GGA AAT GAT CAA TTG GGT ATT GAA CCA GAC    576
Gly Asp Ile Tyr Tyr Ser Gly Asn Asp Gln Leu Gly Ile Glu Pro Asp
            180                 185                 190

AAA GAT AAG GCG ATT GTC TAT TAT AAA ATG GCG GCT GAT ATG AGT TCT    624
Lys Asp Lys Ala Ile Val Tyr Tyr Lys Met Ala Ala Asp Met Ser Ser
        195                 200                 205

TCT AGG GCT TAT GAA GGG TTA GCA GAG TCT TAT CGG TAT GGG TTA GGC    672
Ser Arg Ala Tyr Glu Gly Leu Ala Glu Ser Tyr Arg Tyr Gly Leu Gly
    210                 215                 220

GTG GAA AAA GAT AAG AAA AAG GCT GAA GAA TAC ATG CAA AAA GCA TGC    720
Val Glu Lys Asp Lys Lys Lys Ala Glu Glu Tyr Met Gln Lys Ala Cys
225                 230                 235                 240

GAT TTT GAC ATT GAT AAA AAT TGT AAG AAA AAG AAC ACT TCA AGC CGA    768
Asp Phe Asp Ile Asp Lys Asn Cys Lys Lys Lys Asn Thr Ser Ser Arg
                245                 250                 255

TAA                                                                771
```

(2) INFORMATION FOR SEQ ID NO:8:

(i) SEQUENCE CHARACTERISTICS:
        (A) LENGTH: 256 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Tyr Ala Ser Lys Leu Ala Leu Lys Ile Cys Leu Ala Ser Leu
1               5                   10                  15

Cys Leu Phe Ser Ala Leu Gly Ala Glu His Leu Glu Gln Lys Arg Asn
                20                  25                  30

Tyr Ile Tyr Lys Gly Glu Glu Ala Tyr Asn Asn Lys Glu Tyr Glu Arg
            35                  40                  45

Ala Ala Ser Phe Tyr Lys Ser Ala Ile Lys Asn Gly Glu Pro Leu Ala
        50                  55                  60

Tyr Val Leu Leu Gly Ile Met Tyr Glu Asn Gly Arg Gly Val Pro Lys
65                  70                  75                  80

Asp Tyr Lys Lys Ala Glu Tyr Phe Gln Lys Ala Val Asp Asn Asp
                85                  90                  95

Ile Pro Arg Gly Tyr Asn Asn Leu Gly Val Met Tyr Lys Glu Gly Arg
                100                 105                 110

Gly Val Pro Lys Asp Glu Lys Lys Ala Val Glu Tyr Phe Arg Ile Ala
            115                 120                 125

Thr Glu Lys Gly Tyr Ala Asn Ala Tyr Ile Asn Leu Gly Ile Met Tyr
        130                 135                 140

Met Glu Gly Arg Gly Val Pro Ser Asn Tyr Val Lys Ala Thr Glu Cys
145                 150                 155                 160

Phe Arg Lys Ala Met His Lys Gly Asn Val Glu Ala Tyr Ile Leu Leu
                165                 170                 175

Gly Asp Ile Tyr Tyr Ser Gly Asn Asp Gln Leu Gly Ile Glu Pro Asp
            180                 185                 190
```

```
Lys Asp Lys Ala Ile Val Tyr Tyr Lys Met Ala Ala Asp Met Ser Ser
        195                 200                 205

Ser Arg Ala Tyr Glu Gly Leu Ala Glu Ser Tyr Arg Tyr Gly Leu Gly
        210                 215                 220

Val Glu Lys Asp Lys Lys Ala Glu Glu Tyr Met Gln Lys Ala Cys
225                 230                 235                 240

Asp Phe Asp Ile Asp Lys Asn Cys Lys Lys Asn Thr Ser Ser Arg
                245                 250                 255

(2) INFORMATION FOR SEQ ID NO:9:

(i) SEQUENCE CHARACTERISTICS:
        (A) LENGTH: 528 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Helicobacter pylori (vii) IMMEDIATE SOURCE:
        (B) CLONE: Clone B4.6

(ix) FEATURE:
        (A) NAME/KEY: CDS
        (B) LOCATION: 1..525

(xi) SEQUENCE DESCRIPTION: SEQ ID NO:9:

ATG AAA AAT CAA GTT AAA AAA ATT TTA GGA ATG AGT GTG ATA GCA GCG        48
Met Lys Asn Gln Val Lys Lys Ile Leu Gly Met Ser Val Ile Ala Ala
 1               5                  10                  15

ATG GTG ATC GTA GGT TGT AGC CAT GCC CCA AAA TCA GGT ATC AGC AAA        96
Met Val Ile Val Gly Cys Ser His Ala Pro Lys Ser Gly Ile Ser Lys
                20                  25                  30

AGC AAT AAG GCT TAC AAA GAA GCG ACT AAA GGC GCT CCT GAT TGG GTA       144
Ser Asn Lys Ala Tyr Lys Glu Ala Thr Lys Gly Ala Pro Asp Trp Val
        35                  40                  45

GTA GGG GAT TTG GAA AAA GTG GCG AAG TAT GAA AAA TAT TCA GGG GTC       192
Val Gly Asp Leu Glu Lys Val Ala Lys Tyr Glu Lys Tyr Ser Gly Val
    50                  55                  60

TTT TTA GGA AGG GCT GAG GAT TTG ATC ACT AAT AAT GAT GTG GAT TAT       240
Phe Leu Gly Arg Ala Glu Asp Leu Ile Thr Asn Asn Asp Val Asp Tyr
65                  70                  75                  80

TCT ACT AAC CAA GCT ACA GCG AAA GCT AGG GCT AAT TTA GCG GCG AAT       288
Ser Thr Asn Gln Ala Thr Ala Lys Ala Arg Ala Asn Leu Ala Ala Asn
                85                  90                  95

CTA AAA TCC ACT TTA CAA AAA GAT TTG GAA AAC GAA AAA ACT AGA ACG       336
Leu Lys Ser Thr Leu Gln Lys Asp Leu Glu Asn Glu Lys Thr Arg Thr
            100                 105                 110

GTA GAC GCT TCT GGT AAA AGG TCC ATC AGC GGC ACT GAT ACT GAA AAA       384
Val Asp Ala Ser Gly Lys Arg Ser Ile Ser Gly Thr Asp Thr Glu Lys
        115                 120                 125

ATT TCT CAA TTA GTG GAT AAG GAA TTG ATC GCT TCT AAA ATG CTT GCC       432
Ile Ser Gln Leu Val Asp Lys Glu Leu Ile Ala Ser Lys Met Leu Ala
    130                 135                 140

CGC TAT GTT GGT AAA GAT AGG GTT TTT GTT TTA GTG GGC TTG GAT AAG       480
Arg Tyr Val Gly Lys Asp Arg Val Phe Val Leu Val Gly Leu Asp Lys
145                 150                 155                 160

CAA ATT GTG GAT AAA GTG CGC GAA GAG TTG GGC ATG GTT AAA AAG           525
Gln Ile Val Asp Lys Val Arg Glu Glu Leu Gly Met Val Lys Lys
                165                 170                 175
```

TAG                                                                528

(2) INFORMATION FOR SEQ ID NO:10:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO:10:

Met Lys Asn Gln Val Lys Lys Ile Leu Gly Met Ser Val Ile Ala Ala
 1               5                  10                  15

Met Val Ile Val Gly Cys Ser His Ala Pro Lys Ser Gly Ile Ser Lys
            20                  25                  30

Ser Asn Lys Ala Tyr Lys Glu Ala Thr Lys Gly Ala Pro Asp Trp Val
            35                  40                  45

Val Gly Asp Leu Glu Lys Val Ala Lys Tyr Glu Lys Tyr Ser Gly Val
        50                  55                  60

Phe Leu Gly Arg Ala Glu Asp Leu Ile Thr Asn Asn Asp Val Asp Tyr
65                  70                  75                  80

Ser Thr Asn Gln Ala Thr Ala Lys Ala Arg Ala Asn Leu Ala Ala Asn
                85                  90                  95

Leu Lys Ser Thr Leu Gln Lys Asp Leu Glu Asn Glu Lys Thr Arg Thr
                100                 105                 110

Val Asp Ala Ser Gly Lys Arg Ser Ile Ser Gly Thr Asp Thr Glu Lys
            115                 120                 125

Ile Ser Gln Leu Val Asp Lys Glu Leu Ile Ala Ser Lys Met Leu Ala
130                 135                 140

Arg Tyr Val Gly Lys Asp Arg Val Phe Val Leu Val Gly Leu Asp Lys
145                 150                 155                 160

Gln Ile Val Asp Lys Val Arg Glu Glu Leu Gly Met Val Lys Lys
                165                 170                 175

(2) INFORMATION FOR SEQ ID NO:11:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: N-terminal (vi) ORIGINAL SOURCE:
        (A) ORGANISM: Helicobacter pylori (xi) SEQUENCE DESCRIPTION: SEQ ID NO:11:

Met Lys Lys Ile Ser Arg Lys Glu Tyr Val
 1               5                  10

(2) INFORMATION FOR SEQ ID NO:12:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: N-terminal

```
    (vi) ORIGINAL SOURCE:
         (A) ORGANISM: Helicobacter pylori (xi) SEQUENCE DESCRIPTION: SEQ ID NO:12:

Met Lys Leu Thr Pro Lys Glu Leu Asp Lys Leu Met Leu His Arg Ala
1               5                   10                  15

Gly Glu (2) INFORMATION FOR SEQ ID NO:13:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: N-terminal (vi) ORIGINAL SOURCE:
         (A) ORGANISM: Helicobacter pylori (xi) SEQUENCE DESCRIPTION: SEQ ID NO:13:

Met Leu Asn Gln Val Leu Leu Lys Leu Gly Met Ser Val Lys Ala Ala
1               5                   10                  15

Met Val (2) INFORMATION FOR SEQ ID NO:14:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: N-terminal (vi) ORIGINAL SOURCE:
         (A) ORGANISM: Helicobacter pylori (xi) SEQUENCE DESCRIPTION: SEQ ID NO:14:

Met Ile Ser Lys Glu Glu Val Leu Glu Tyr Ile Gly Ser Leu Ser
1               5                   10                  15

(2) INFORMATION FOR SEQ ID NO:15:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (vi) ORIGINAL SOURCE:
         (A) ORGANISM: Helicobacter pylori (xi) SEQUENCE DESCRIPTION: SEQ ID NO:15:

Ala Lys Glu Ile Lys Phe Val Asp Ala Ala Arg Asn Leu Phe Phe
1               5                   10                  15

(2) INFORMATION FOR SEQ ID NO:16:

(i) SEQUENCE CHARACTERISTICS:
        (A) LENGTH: 15 amino acids
        (B) TYPE: amino acid
        (D) TOPOLOGY: linear (ii) MOLECULE TYPE: peptide
```

(v) FRAGMENT TYPE: N-terminal (vi) ORIGINAL SOURCE:
            (A) ORGANISM: Helicobacter pylori (xi) SEQUENCE DESCRIPTION: SEQ ID NO:16:

Met Phe Gly Phe Lys Gln Leu Gln Leu Gln Phe Ser Gln Lys Val
1               5                   10                  15

(2) INFORMATION FOR SEQ ID NO:17:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: NO (xi) SEQUENCE DESCRIPTION: SEQ ID NO:17:

CGCCCGGGAT GAAAAATCAA GTTAAAAAAA TT                                            32

(2) INFORMATION FOR SEQ ID NO:18:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: YES (xi) SEQUENCE DESCRIPTION: SEQ ID NO:18:

GCAGATCTAA CCTACTTTTA ACCATGCCCA A                                             31

(2) INFORMATION FOR SEQ ID NO:19:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: NO (xi) SEQUENCE DESCRIPTION: SEQ ID NO:19:

GGGCCCGGGA TGGCAATTTC AAAAGAAG                                                 28

(2) INFORMATION FOR SEQ ID NO:20:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: YES (xi) SEQUENCE DESCRIPTION: SEQ ID NO:20:

GGGGTCGACT AAGATCTCTT GACTTCAACC TTAGCG                                        36

(2) INFORMATION FOR SEQ ID NO:21:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (xi) SEQUENCE DESCRIPTION: SEQ ID NO:21:

GCGCCCCGGG ATGTCAAATA GCATGTTGGA TAAAAATAAA                    40

(2) INFORMATION FOR SEQ ID NO:22:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (xi) SEQUENCE DESCRIPTION: SEQ ID NO:22:

GCGCAGATCT AGGTTTAATG GTAACTAACA CGCTCATCCG                    40

(2) INFORMATION FOR SEQ ID NO:23:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (xi) SEQUENCE DESCRIPTION: SEQ ID NO:23:

CATGCCATGG GCTTTGGGAA TAAGCAGTTG CAAC                            34

(2) INFORMATION FOR SEQ ID NO:24:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (xi) SEQUENCE DESCRIPTION: SEQ ID NO:24:

CGGAATTCTC ATTCGCCTTT TTGAATTTTT TCAATG                        36

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

```
        (iv) ANTI-SENSE: NO (xi) SEQUENCE DESCRIPTION: SEQ ID NO:25:

CATGCCATGG GATACGCAAG CAAATTAGCC                                              30

(2) INFORMATION FOR SEQ ID NO:26:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: DNA (genomic)

(iv) ANTI-SENSE: YES (xi) SEQUENCE DESCRIPTION: SEQ ID NO:26:

CGGAATTCTT ATCGGCTTGA AGTGTTCTTT TTC                                          33
```

PROTECTIVE HELICOBACTER ANTIGENS

This application is a national phase application based on PCT/AU96/00225, filed Apr. 19, 1996, which claims priority to PN 2575, filed Apr. 21, 1995, PN 3931, filed Jul. 3, 1995, and PN 7565, filed Jan. 16, 1996.

FIELD OF THE INVENTION

This invention relates to protective Helicobacter antigens, especially *H. pylori* antigens, and in particular to the use of these antigens for the treatment of, or prevention of, gastroduodenal disease associated with *H. pylori* infection.

BACKGROUND OF THE INVENTION

*Helicobacter pylori* is a gram negative, spiral bacterium which infects the lining of the human stomach. It is widely distributed, chronically infecting perhaps half the world's population. The bacterium spreads from person to person by oral-oral or faecal-oral transmission, there being no recognised environmental reservoir.

Infection with the bacterium causes an inflammation of the gastric mucosa, or stomach lining. Usually this does not resolve, and infection and inflammation are believed to persist for many decades. Often this is not associated with symptoms, however this chronic infection is associated with an increased risk of a number of sequelae. A significant portion of those infected develop peptic ulceration of the duodenum or stomach, when the infection process disrupts the usual protective mechanisms the stomach has against its own digestive products. Also, long periods of infection increase the risk of the development of adenocarcinomas or lymphomas of the stomach wall.

Therefore, prevention or treatment of *H. pylori* infection has the potential to prevent considerable mortality and morbidity resulting from the sequelae of chronic infection.

In early experiments, *H. pylori* did not infect conventional laboratory animals. However, a laboratory mouse model of *H. pylori* infection, using the closely related organism, *Helicobacter felis*, has been developed (Lee et al., 1990; Dick-Hegedus and Lee, 1991). This model has proven very useful in screening new antimicrobial therapeutic regimes.

*H. felis* is a spiral shaped bacterium that shares a very close DNA homology with *H. pylori*. The bacterium colonises the mouse stomach in a similar manner to the way that *H. pylori* colonises the human stomach. The main ecological niche is gastric mucus, and colonisation is mainly seen in the antrum of the stomach. In germfree mice, *H. felis* infection induces a gastritis that is very similar to the human *H. pylori* infection, with a chronic inflammation of mononuclear cells accompanied by a polymorphonuclear leucocyte infiltration. Infection with either organism results in the induction of a similar raised systemic humoral immune response against *H. pylori* and *H. felis* respectively (Lee et al., 1990).

The *H. felis* model has proved to be very predictive of the efficacy of anti-*H. pylori* therapy in humans. Thus, monotherapy with agents with high in vitro activity such as erythromycin show no significant in vivo effect against *H. felis* in mice, just as erythromycin has no ant-*H. pylori* effect in humans, despite its high antimicrobial effects in vitro. In contrast, the triple therapy regimens of a bismuth compound, metronidazole, and tetracycline or amoxycillin lead to a very high eradication rate in *H. felis* infected mice (Dick-Hegedus and Lee, 1991). Such therapies are among the most successful human anti-*H. pylori* regimens.

The *H. felis* model has also been used to demonstrate that mice can be orally immunised with Helicobacter antigens, either to protect them from becoming infected (Chen et al, 1992), or to treat them when they are already infected so as to eradicate the infection (Doidge et al, 1994). Antigens that have been used in these vaccines include disrupted cellular preparations from either *H. felis* or *H. pylori*, and the bacterial enzyme urease from *H. felis* or *H. pylori* or subunits thereof, produced from *E. coli* clones expressing all or part of the *H. pylori* urease molecule (Michetti et al, 1994; see also International Patent Publications Nos. WO 90/04030, WO 93/07273 and WO 94/09823). *H. pylori* heat shock protein (Hsp or HSP) has also been shown to be a protective antigen (Ferrero et al., 1995).

International Patent Publication No. WO 93/18150 (Application No. PCT/EP93/00472) discloses vaccines or therapeutic compositions comprising one or more of recombinant *H. pylori* cytotoxin (CT or VacA), *H. pylori* cytotoxin-associated immunodominant antigen (CAI or CagA) or *H. pylori* heat shock protein, optionally together with *H. pylori* urease. International Patent Publication No. WO 95/27506 (Application No. PCT/FR95/00383) discloses an anti-*H. pylori* immunising composition containing a substantially purified *H. pylori* catalase as the active ingredient; and International Patent Publication No. WO 95/14093 (Application No. PCT/EP93/03259) discloses an immunogenic composition capable of inducing protective antibodies against Helicobacter infection which comprises at least one urease structural polypeptide from *H. pylori* or *H. felis* and optionally a urease-associated heat shock protein or chaperonin from Helicobacter.

The fact that antigens derived from *H. pylori* can be used to protect mice from *H. felis* infection suggests that there are cross-reactive, and cross-protective antigens between the two species. That is, that there are molecules present in *H. pylori*, which can induce immune responses in mice that recognise targets on *H. felis*, thus protecting the mice from *H. felis* infection. If an immune response to these *H. pylori* molecules will protect mice from *H. felis* infection, it is likely that similar immune responses will protect humans from *H. pylori* infection, or if already infected, cure them of it. Urease has been demonstrated to be such a cross-protective molecule in the *H. felis* mouse model (Michetti et al, 1994).

In work leading to the present invention, in order to identify further cross-reactive and cross protective antigens, a DNA library from an *H. pylori* strain has been constructed and screened with serum from mice that had been orally immunised with a vaccine prepared from disrupted *H. felis* cells and a mucosal adjuvant, with the aim of identifying *E. coli* clones expressing *H. pylori* proteins recognised by anti-*H. felis* antibodies and of subsequently identifying the antigenic protective *H. pylori* proteins.

SUMMARY OF THE INVENTION

In one aspect, the present invention provides an antigenic preparation for use in the treatment or prevention of Helicobacter infection in a mammalian host, which comprises an at least partially purified preparation of at least one Helicobacter antigen selected from the group consisting of:

(i) an antigen having a molecular mass of approximately 19 kDa which is processed into a mature form having a molecular mass of approximately 17 kDa;

(ii) an antigen having a molecular mass of approximately 13 kDa;

(iii) an antigen having a molecular mass of approximately 36 kDa;

(iv) an antigen having a molecular mass of approximately 50 kDa;

(v) an antigen having a molecular mass of approximately 29 kDa; and (vi) immunogenic fragments of any of antigens (i) to (v) above which are capable of eliciting a specific protective immune response in a mammalian host.

In another aspect, the present invention provides an isolated Helicobacter antigen for use in the treatment or prevention of Helicobacter infection in a mammalian host, selected from the group consisting of:

(i) an antigen having a molecular mass of approximately 19 kDa which is processed into a mature form having a molecular mass of approximately 17 kDa;

(ii) an antigen having a molecular mass of approximately 13 kDa;

(iii) an antigen having a molecular mass of approximately 36 kDa;

(iv) an antigen having a molecular mass of approximately 50 kDa; and (v) an antigen having a molecular mass of approximately 29 kDa; and (vi) immunogenic fragments of any of antigens (i) to (v) above which are capable of eliciting a specific protective immune response in a mammalian host.

Each of the above antigens is further characterised by being reactive with anti-*H. felis* antibodies.

Preferably, antigen (i) above comprises an amino acid sequence substantially corresponding to the deduced sequence of clone B4.6 hereinafter (SEQ ID NO.10), or allelic or other variants thereof; antigen (ii) above comprises an amino acid sequence substantially corresponding to the deduced sequence of clone C3.5 hereinafter (SEQ ID NO.2), or allelic or other variants thereof; antigen (iii) above comprises an amino acid sequence substantially corresponding to the deduced sequence of clone E2.5 hereinafter (SEQ ID NO.4), or allelic or other variants thereof; antigen (iv) above comprises an amino acid sequence substantially corresponding to the deduced sequence of clone G3.8 hereinafter (SEQ ID NO. 6), or allelic or other variants thereof; and antigen (v) above comprises an amino acid sequence substantially corresponding to the deduced sequence of clone H5.1 hereinafter (SEQ ID NO. 8), or allelic or other variants thereof.

Suitable variants may have at least 50–60%, more preferably at least 70–80%, and most preferably at least 90%, similarity to one of the amino acid sequences referred to above, or to a region or part thereof, provided the variant is capable of eliciting a specific protective immune response in a mammalian host.

The term "at least partially purified" as used herein denotes a preparation in which the content of the particular antigen is greater, preferably at least 30% greater and more preferably at least 50% greater, than the content of the antigen in a whole cell sonicate of Helicobacter bacteria. Preferably, the preparation is one in which the antigen is "substantially pure", that is one in which the content of the particular antigen is at least 80%, more preferably at least 90%, of the total Helicobacter antigens in the preparation.

The term "isolated" as used herein denotes that the antigen has undergone at least one purification or isolation step, and preferably the antigen is in a form suitable for use in a vaccine composition.

It is to be understood that the present invention extends not only to the particular antigens of Helicobacter bacteria as described above, but also to immunogenic fragments of the particular antigen(s), that is fragments of the antigen(s) which are capable of eliciting a specific protective immune response in a mammalian host. Suitably, the immunogenic fragment will comprise at least five, and more preferably at least ten, contiguous amino acid residues of the particular antigen(s). Such immunogenic fragments may also be recognised by Helicobacter-specific antibodies, particularly antibodies which have a protective or therapeutic effect in relation to Helicobacter infection.

In another aspect, the present invention provides a vaccine composition for use in the treatment or prevention of Helicobacter infection in a mammalian host, which comprises an immunologically effective amount of an antigenic preparation or of an isolated Helicobacter antigen as broadly described above, optionally in association with an adjuvant, together with one or more pharmaceutically acceptable carriers and/or diluents.

In yet another aspect, the present invention provides a method for the treatment or prevention of Helicobacter infection in a mammalian host, which comprises administration to said host of an immunologically effective amount of an antigenic preparation or of an isolated Helicobacter antigen as broadly described above, optionally in association with an adjuvant.

In a related aspect, this invention provides the use of a vaccine composition comprising an immunologically effective amount of an antigenic preparation or of an isolated Helicobacter antigen as broadly described above, optionally in association with an adjuvant, for the treatment or prevention of Helicobacter infection in a mammalian host.

By use of the term "immunologically effective amount" herein, it is meant that the administration of that amount to a mammalian host, either in a single dose or as part of a series, is effective for treatment or prevention of Helicobacter infection. This amount varies depending upon the health and physical condition of the individual to be treated, the taxonomic group of individual to be treated, the capacity of the individual's immune system to synthesise antibodies, the degree of protection desired, the formulation of the vaccine, the assessment of the medical situation, and other relevant factors. It is expected that the amount will fall in a relatively broad range that can be determined through routine trials.

Preferably, but not essentially, the antigenic preparation of this invention is orally administered to the host, and is administered in association with a mucosal adjuvant. However, the invention also extends to parenteral administration of this antigenic preparation.

The present invention also extends to an antibody, which may be either a monoclonal or polyclonal antibody, specific for an antigenic preparation or an isolated Helicobacter antigen as broadly described above. Such antibodies may be produced by methods which are well known to persons skilled in this field.

In this aspect, the invention further provides a method for the treatment or prevention of Helicobacter infection in a mammalian host, which comprises passive immunisation of said host by administration of an effective amount of an antibody, particularly a monoclonal antibody, specific for an antigenic preparation or an isolated Helicobacter antigen as broadly described above.

The Helicobacter antigenic preparation or isolated antigen of this invention may be prepared by purification or isolation from natural sources, such as a whole cell sonicate of Helicobacter bacteria. Alternatively, however the antigenic preparation or isolated antigen may be prepared by synthetic, preferably recombinant, techniques. When prepared by recombinant techniques, the antigen may have an amino acid sequence substantially identical to the naturally occurring sequence or may contain one or more amino acid substitutions, deletions and/or additions thereto provided that following such alterations to the sequence, the molecule is still capable of eliciting a specific protective immune response against the naturally occurring Helicobacter antigen. A similar immunogenic requirement is necessary for any fragments or derivatives of the antigen whether made from the recombinant molecule or the naturally occurring molecule. Accordingly, reference herein to a Helicobacter antigen is considered reference to the naturally occurring molecule, its recombinant form and any mutants, derivatives, fragments, homologues or analogues thereof provided that such molecules elicit a specific protective immune response against the naturally occurring Helicobacter antigen. Also included are fusion molecules between two or more Helicobacter antigens or with other molecules including fusion molecules with other molecules such as glutathione-S-transferase (GST) or β-galactosidase.

The present invention also extends to an isolated nucleic acid molecule encoding a Helicobacter antigen of the present invention, and preferably having a nucleotide sequence as set forth in one of SEQ ID NO. 1, 3, 5, 7 or 9, or being substantially similar to all or a part thereof. The term "substantially similar" means having at least 40–50%, more preferably at least 60–70%, and most preferably at least 80% identity. A "part" in this context means a contiguous series of at least 15 nucleotides, and more preferably at least 25 nucleotides.

According to this embodiment, there is provided a nucleic acid molecule comprising a sequence of nucleotides which encodes a Helicobacter antigen as broadly described above, and hybridises under low stringency conditions to all or part of a nucleic acid sequence set forth in one of SEQ ID NO. 1, 3, 5, 7 or 9, or to a complementary form thereof.

In another aspect, this invention provides a nucleic acid molecule comprising a sequence of nucleotides substantially as set forth in one of SEQ ID NO. 1, 3, 5, 7 or 9, or a part thereof.

The nucleic acid molecule may be RNA or DNA, single stranded or double stranded, in linear or covalently closed circular form. For the purposes of defining the level of stringency, reference can conveniently be made to Manratis, et al. (1982) which is herein incorporated by reference where the washing step at paragraph 11 is considered high stringency. A low stringency is defined herein as being in 0.1–0.5 w/v SDS at 37–45° C. for 2–3 hours. Depending on the source and concentration of nucleic acid involved in the hybridisation, alternative conditions of stringency may be employed such as medium stringent conditions which are considered herein to be 0.25–0.5% w/v SDS at ±45° C. for 2–3 hours or high stringent conditions as disclosed by Maniatis, et al. (1982).

It will be appreciated that the sequence of nucleotides of this aspect of the invention may be obtained from natural, synthetic or semi-synthetic sources; furthermore, this nucleotide sequence may be a naturally-occurring sequence, or it may be related by mutation, including single or multiple base substitutions, deletions, insertions and inversions, to such a naturally-occurring sequence, provided always that the nucleic acid molecule comprising such a sequence is capable of being expressed as a Helicobacter antigen as broadly described above.

The nucleotide sequence may have expression control sequences positioned adjacent to it, such control sequences usually being derived from a heterologous source.

This invention also provides a recombinant DNA molecule comprising an expression control sequence having promoter sequences and initiator sequences and a nucleotide sequence which codes for a Helicobacter antigen, the nucleotide sequence being located 3' to the promoter and initiator sequences. In yet another aspect, the invention provides a recombinant DNA cloning vehicle capable of expressing a Helicobacter antigen comprising an expression control sequence having promoter sequences and initiator sequences, and a nucleotide sequence which codes for a Helicobacter antigen, the nucleotide sequence being located 3' to the promoter and initiator sequences. In a further aspect, there is provided a host cell containing a recombinant DNA cloning vehicle and/or a recombinant DNA molecule as described above.

Suitable expression control sequences and host cell/cloning vehicle combinations are well known in the art, and are described by way of example, in Sambrook et al. (1989).

In yet further aspects, there is provided fused polypeptides comprising a Helicobacter antigen of this invention and an additional polypeptide, for example a polypeptide coded for by the DNA of a cloning vehicle, fused thereto. Such a fused polypeptide can be produced by a host cell transformed or infected with a recombinant DNA cloning vehicle as described above, and it can be subsequently isolated from the host cell to provide the fused polypeptide substantially free of other host cell proteins.

The present invention also extends to synthetic polypeptides displaying the antigenicity of a Helicobacter antigen of this invention. As used herein, the term "synthetic" means that the polypeptides have been produced by chemical or biological means, such as by means of chemical synthesis or by recombinant DNA techniques leading to biological synthesis. Such polypeptides can, of course, be obtained by cleavage of a fused polypeptide as described above and separation of the desired polypeptide from the additional polypeptide coded for by the DNA of the cloning vehicle by methods well known in the art. Alternatively, once the amino acid sequence of the desired polypeptide has been established, for example, by determination of the nucleotide sequence coding for the desired polypeptide, the polypeptide may be produced synthetically, for example by the well-known Merrifield solid-phase synthesis procedure.

Once recombinant DNA cloning vehicles and/or host cells expressing a Helicobacter antigen of this invention have been identified, the expressed polypeptides synthesised by the host cells, for example, as a fusion protein, can be isolated substantially free of contaminating host cell components by techniques well known to those skilled in the art.

Isolated polypeptides comprising, or containing in part, amino acid sequences corresponding to a Helicobacter antigen may be used to raise polyclonal antisera by immunising rabbits, mice or other animals using well established procedures. Alternatively, such polypeptides may be used in the preparation of monoclonal antibodies by techniques well known in the art.

In addition, the polypeptides in accordance with this invention including fused polypeptides may be used as an active immunogen in the preparation of single or multivalent vaccines by methods well known in the art of vaccine manufacture for use in the treatment or prevention of Helicobacter infection in a mammalian host.

Alternatively, the polypeptides in accordance with the present invention including fused polypeptides may be used as antigen in a diagnostic immunoassay for detection of antibodies to Helicobacter in a sample, for example, a serum sample from a human or other mammalian patient. Such immunoassays are well known in the art, and include assays such as radioimmunoassays (RIA) and enzyme-linked immunosorbent assays (ELISA).

Throughout this specification, unless the context requires otherwise, the word "comprise", or variations such as "comprises" or "comprising", is to be understood to imply the inclusion of a stated integer or group of integers but not the exclusion of any other integer or group of integers.

DETAILED DESCRIPTION OF THE INVENTION

Preferably, the antigenic preparation or isolated antigen of this invention comprises *H. pylori* or *H. felis* antigen(s). Preferably also, this antigenic preparation or isolated antigen is used in a vaccine composition for oral administration which includes a mucosal adjuvant.

In a particularly preferred aspect of this invention, an oral vaccine composition comprising an antigenic preparation or isolated antigen comprising *H. pylori* antigen(s) as broadly described above, in association with a mucosal adjuvant, is used for the treatment or prevention of *H. pylori* infection in a human host.

The mucosal adjuvant which is optionally, and preferably, administered to the infected host with the Helicobacter antigenic preparation of this invention, is preferably cholera toxin. Mucosal adjuvants other than cholera toxin which may be used in accordance with the present invention include non-toxic derivatives of cholera toxin, such as the B sub-unit (CTB), chemically modified cholera toxin, or related proteins produced by modification of the cholera toxin amino acid sequence. These may be added to, or conjugated with, the Helicobacter antigenic preparation. The same techniques can be applied to other molecules with mucosal adjuvant or delivery properties such as *Escherichia coli* heat labile toxin. Other compounds with mucosal adjuvant or delivery activity may be used such as bile; polycations such as DEAE-dextran and polyornithine; detergents such as sodium dodecyl benzene sulphate; lipid-conjugated materials; antibiotics such as streptomycin; vitamin A; and other compounds that alter the structural or functional integrity of mucosal surfaces. Other mucosally active compounds include derivatives of microbial structures such as MDP; acridine and cimetidine.

The Helicobacter antigenic preparation or isolated antigen of this invention may be delivered in accordance with this invention in ISCOMS™ (immune stimulating complexes), ISCOMS™ containing CTB, liposomes or encapsulated in compounds such as acrylates or poly(DL-lactide-co-glycoside) to form microspheres of a size suited to adsorption by M cells. Alternatively, micro or nanoparticles may be covalently attached to molecules such as vitamin B12 which have specific gut receptors. The Helicobacter antigenic preparation or isolated antigen may also be incorporated into oily emulsions and delivered orally. An extensive though not exhaustive list of adjuvants can be found in Cox and Coulter, (1992).

Other adjuvants, as well as conventional pharmaceutically acceptable carriers, excipients, buffers or diluents, may also be included in the prophylactic or therapeutic vaccine composition of this invention. The vaccine composition may, for example, be formulated in enteric coated gelatine capsules including sodium bicarbonate buffers together with the Helicobacter antigenic preparation or isolated antigen and cholera toxin mucosal adjuvant.

The formulation of such prophylactic or therapeutic vaccine compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences,* 18th Edition, Mack Publishing Company, Pennsylvania, USA. Except insofar as any conventional media or agent is incompatible with the active ingredient, use thereof in the vaccine compositions of the present invention is contemplated. Supplementary active ingredients can also be incorporated into the compositions.

The Helicobacter antigenic preparation or isolated antigen of the present invention may be administered as the sole active immunogen in a vaccine composition. Alternatively, however, the vaccine composition may include other active immunogens, including other Helicobacter antigens such as urease, lipopolysaccharide, Hsp60, VacA, CagA or catalase, as well as immunologically active antigens against other pathogenic species.

As an alternative to the delivery of the Helicobacter antigenic preparation or isolated antigen in the form of a therapeutic or prophylactic vaccine composition, the antigen or an immunogenic fragment thereof may be delivered to the mammalian host using a live vaccine vector, in particular using live recombinant bacteria, viruses or other live agents, containing the genetic material necessary for the expression of the antigen of immunogenic fragment as a foreign polypeptide. Particularly, bacteria that colonise the gastrointestinal tract, such as Salmonella, Shigella, Yersinia, Vibrio, Escherichia and BCG have been developed as vaccine vectors, and these and other examples are discussed by Holmgren et al. (1992) and McGhee et al.(1992).

Accordingly, the present invention also extends to delivery to the host using a vaccine vector expressing an isolated Helicobacter antigen as broadly described above, or an immunogenic fragment thereof. Accordingly, in a further aspect this invention provides a preparation for use in the treatment or prevention of Helicobacter infection in a mammalian host, which comprises a vaccine vector expressing an isolated Helicobacter antigen as broadly described above, or an immunogenic fragment thereof.

In this aspect, the invention extends to a method for the treatment or prevention of Helicobacter infection in a mammalian host, which comprises administration to said host of a vaccine vector expressing an isolated Helicobacter antigen as broadly described above or an immunogenic fragment thereof.

Further, the invention extends to the use of a vaccine vector expressing an isolated Helicobacter antigen as broadly described above, or an immunogenic fragment thereof, for the treatment or prevention of Helicobacter infection in a mammalian host.

Further features of the present invention are more fully described in the following Examples. It is to be understood, however, that this detailed description is included solely for the purposes of exemplifying the present invention, and should not be understood in any way as a restriction on the broad description of the invention as set out above.

Figure 1:
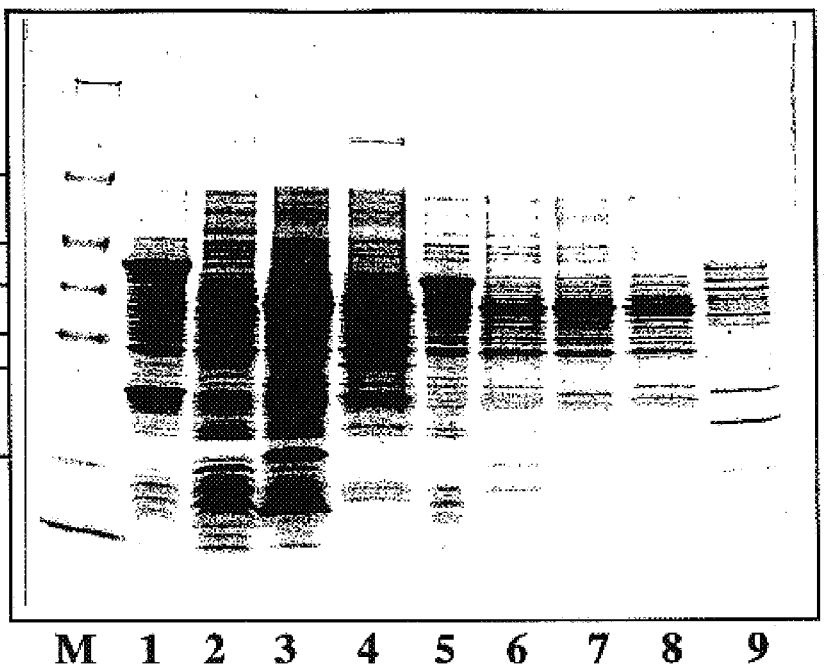
FIGS. 1A and B, 2A and B show cloned *H. pylori* proteins expressed from *E.coli* XLOLR.
Figure 1:
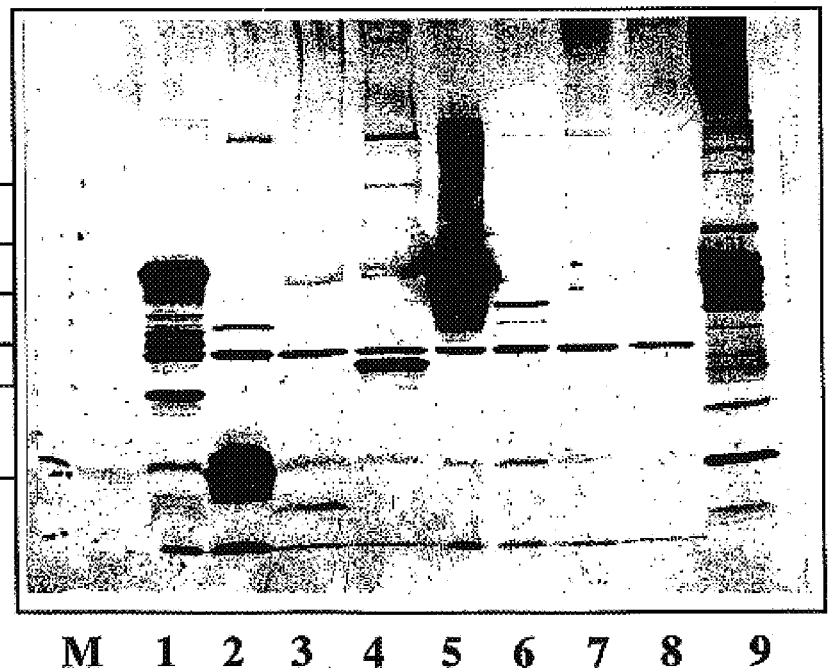

(1A) analysed on 4–20% gradient SDS-polyacrylamide gels, and visualised by CBB stain. Lane M, Molecular weight standards (kDa); Lane 1, Family A; Lane 2, Family B; Lane 3, Family C; Lane 4, uncharacterized protein; Lane 5, Family F; Lane 6, Family G; Lane 7, Family H; Lane 8, Negative Control, E.coli XLOLR; Lane 9, Positive Control, Helicobacter pylori total cell proteins;

(1B) corresponding Western blot samples, lane order the same as for panel A; analyzed on 4–20% gradient SDS-polyacrylamide gels, and visualized by CBB stain. Lane M, Molecular weight standards (kDa); Lanes 1 and 3, uncharacterized protein, Lane 2, Famile E; Lane between lanes 3 and 4, uncharacterized protein; lane 4, negative control.

(2B) corresponding Western Blot samples, lane order the same as for panel A.

EXAMPLE 1

Identification of E.coli clones expressing H. pylori proteins recognised by anti-H. felis antibodies.

A. Materials and Methods

Bacterial strains

*Helicobacter pylori* strain HP921023 was used as the DNA donor for preparing the gene library. *Escherichia coli* strain ER1793 (New England Biolabs) was the host used for phage infection and plating of Lambda ZAP Express. *E.coli* strains XL1-Blue MRF' and XLOLR (Stratagene) were used for excision of phagemid pBK-CMV and protein expression of cloned genes.

Isolation of *H. pylori* chromosomal DNA

Whole cell DNA from *H.pylori* was prepared essentially as reported by Majewski and Goodwin (1988).

Anti-sera preparation

Mouse anti-sera was raised against *Helicobacter felis* by four ora-gastric immunisations at weekly intervals. Each vaccine dose consisted of 1 mg (protein) of sonicated *H. felis* cells and 10 ug of cholera toxin. Blood was collected and serum pooled. This serum was adsorbed with 50% v/v *E.coli* extract (Promega) containing 5% w/v skim milk and 0.05% v/v Tween 20 in TBS at a final dilution of 1:100. The preparation was incubated at room temperature for 4 hours prior to immunoscreening to eliminate or reduce nonspecific reactivity of antisera with host proteins. The specificity of the sera was confirmed by dot blot and Western blotting, using dilutions of whole cells of *H. pylori* for positive control and *E.coli* XLOLR as the negative control.

Bacterial growth conditions

For infection with Lambda ZAP Express, strain ER1793 cells were initially grown in Luria-Bertani (LB) broth supplemented with 0.2% w/v maltose and 10 mM MgSO4 at 30° C. Following infection, cells were maintained in LB broth at 37° C. for 15 minutes and then plated on NZY agar medium and incubated at 42° C. for 4 hours then at 37° C. overnight. For phagemid excision and plasmid isolation *E.coli* strains XL1-Blue and XLOLR were grown in LB broth at 37° C., and transformed XLOLR cells selected on LB/Kanamycin plates (50 µg/ml) at 37° C.

Construction of *H. pylori* gene library

An *H.pylori* expression library was constructed, using standard procedures (Sambrook et al, 1989), in the Lambda ZAP Express vector (Stratagene) which had been predigested with BamHI and the terminal 5' phosphates removed with calf intestinal phosphatase. Genomic DNA partially digested with Sau3AI, was fractionated by gel electrophoresis and DNA fragments between 6 to 12 kb were isolated. This DNA was ligated with 1.0 µg of BamH1-digested lambda arms. Recombinant phage DNA was packaged in vitro using Gigapack II extract (Stratagene). The library was titrated by infecting *E.coli* strain ER1793 or XL1-Blue MRF' cells with aliquots of packaged phage and plated onto indicator plates containing IPTG and X-Gal. The ratio of nonrecombinant phage to recombinant phage was 1:5. The titre of the recombinant library was calculated to be $1 \times 10^6$ pfu per µg of lambda DNA.

Antibody screening of *H.pylori* genomic library

A portion of the library was screened by plaque immunoblot assay. A total of 10,000 plaques were plated (2,000 bacteriophage plaques per plate), and lifted onto Hybond-C extra nitrocellulose filters (Amersham) to be processed as per Sambrook et al (1989). The filters were screened with a 1:100 dilution of anti-*H. felis* mouse sera, at room temperature overnight. After being washed in 0.05% v/v Tween 20 in TBS, filters were incubated in 1:2000 conjugated goat anti-mouse immunoglobulin G-conjugated horse radish peroxidase for 1.5 hours. Filters were washed as previously described above and the colour reaction was developed with TMB substrate (KPL Inc.). When a positive phage clone was identified, an agar plug containing the plaque was picked and phage eluted into SM buffer. To obtain plaque purity the process of infecting bacteria, replating and immunoscreening was repeated.

In vivo excision of plasmid pBK-CMV from Lambda ZAP Express vector

In vivo excision of pBK-CMV containing *H.pylori* DNA from Lambda ZAP Express was achieved by infecting *E.coli* strain XL1-Blue MRF' simultaneously with Lambda ZAP Express containing insert DNA and ExAssist helper phage M13. Excised phagemids were packaged as filamentous phage particles and secreted from host cells, which were subsequently heat killed. The phagemids were rescued by infecting XLOLR cells and plating onto LB/Kanamycin (50 µg/ml) plates. Bacterial colonies appearing on plates contained pBK-CMV double-stranded phagemid with the cloned DNA insert from *H.pylori*. These colonies were then analysed for protein expression.

SDS-PAGE and Western blot analysis of proteins

The total proteins produced by cloned *H. pylori* DNA in *E.coli* XLOLR were analysed by standard SDS-PAGE and Western Blot techniques (Sambrook et al 1989; Towbin et al 1979). 10 ml cultures of XLOLR containing expression plasmid were grown in supermedium at 37° C. overnight. Cultures were divided in two and one induced with IPTG to a final concentration of 1 mM, with continued incubation for 2–4 h. Aliquots of 1 ml were collected, cells pelleted by centrifugation and resuspended in 10 mM Tris-HCl (pH 8). Cells were mixed with equal volume of SDS sample reducing buffer and boiled for 10 minutes. Proteins were resolved by electrophoresis on 4–20% gradient Tris-glycine gels (Novex) and stained with coomassie brilliant blue (CBB). A gel run in parallel was electrotransferred onto nitrocellulose membrane (BioRad), for detection of immunoreactive proteins of *H.pylori* using anti-*H. felis* mouse sera as described above.

For molecular mass estimation, the Coomassie Blue stained wet gel was scanned with a Molecular Dynamics model 300A densitometer and the apparent molecular mass determined relative to standard proteins using Image Quant version 3.3 software.

Protein N-terminal sequence determination

Proteins to be N-terminal sequenced were separated by SDS-PAGE and transferred onto PVDF membrane (Novex) in IxCAPS electroblotting buffer and then stained with 0.1% w/v CBB in 50% v/v methanol, and destained in 50% v/v methanol until protein bands were visible. The bands corresponding to immunopositive proteins identified by western blot, were excised and sequenced. Amino acid sequencing was performed on an Applied Biosystems Inc., model 473A sequencer at the Centre of Animal Biotechnology, School of Veterinary Science, University of Melbourne. Additional sequencing was provided by Auspep Pty. Ltd.

DNA preparation and sibling analysis of clones

Plasmid DNA was isolated by the alkaline lysis method (Sambrook et al, 1989) from cultures of E.coli XLOLR clones carrying different H.pylori DNA inserts. Restriction enzyme digestions were performed as recommended by the enzyme manufacturer (Promega Inc.). Restriction fragments of cloned H. pylori DNA to be used as probes were resolved by gel electrophoresis in 0.8% agarose, stained with ethidium bromide, excised from gel and purified with a Bresaclean kit for nucleic acid purification (Bresatec Ltd). The SalI/NotI fragments of 2.5–7.0 kb in size were labelled with ($^{32}$P)d-ATP using Random Primers DNA labelling kit (Gibco BRL).

For cross-hybridization analysis, to determine related clones, cell suspensions of XLOLR clones were dotted onto nitrocellulose and treated as per the manufacturers protocol (Amersham). Filters were hybridized at 65° C., overnight in a solution containing 2xPE, 1% w/v skim milk and 7% w/v SDS. After hybridisation, filters were subjected to one 15 min wash in 2xSSC, 0.1% w/v SDS, at room temp and two 30 min. washes in 2xSSC, 0.1% w/v SDS at 65° C. The hybridisation results were visualised by autoradiography on Kodak Biomax film.

B. Results and Discussion

In order to clone potential protective antigens of Helicobacter pylori, a genomic library of strain HP921023 was constructed in the lambda expression vector Lambda ZAP Express. The library was screened for immunoreactivity with sera from mice vaccinated with Helicobacter felis in an attempt to detect clones expressing H.pylori antigens that cross-reacted with H. felis antigens. Approximately 10,000 plaques were screened using the anti-H. felis mouse serum. Fifty immunopositive clones with varying signal intensities were recognised by the mouse sera. These were picked, purified and the expression plasmid pBK-CMV excised for further characterisation of the cloned DNA and the encoded proteins. The proteins expressed by these recombinant plasmids were analysed by SDS-PAGE (FIGS. 1A and 2A) and Western blotting (FIGS. 1B and 2B).

Figure 2:
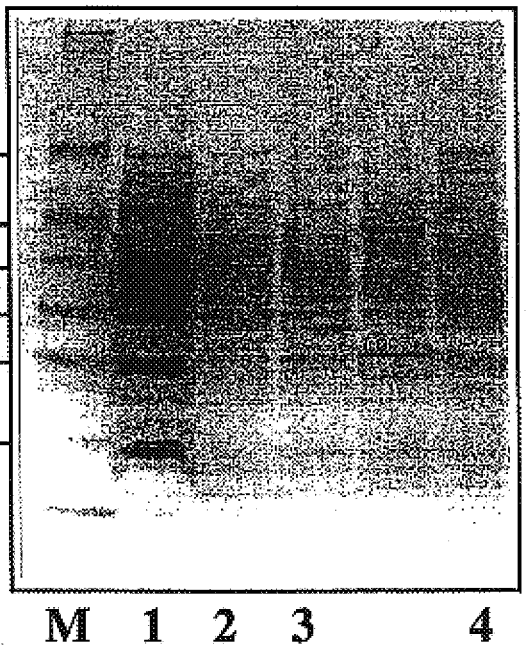
Figure 2:
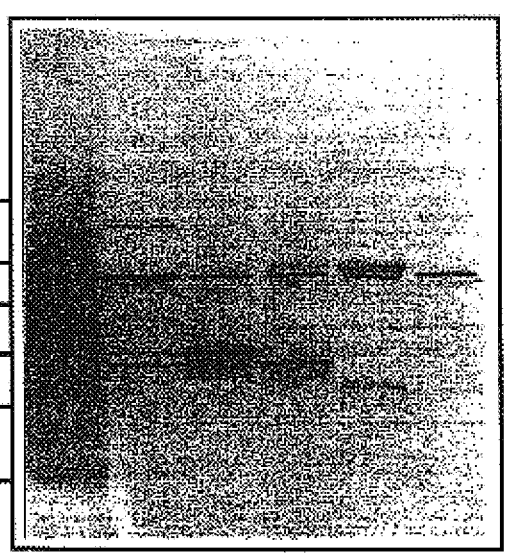

The molecular mass of cloned proteins recognised by the mouse sera ranged from approx. 13 kDa to approx. 62 kDa. A pattern emerged where by clones could be grouped into families based on the protein profile and protein size (see Table 1 below). Families were named alphabetically for convenience (eg.family A, B, C etc.). Family A consists of five members, identified by two predominant proteins of approx. 62 kDa and approx. 33 kDa (FIG. 1B, Lane 1). Family B has 14 related clones expressing two proteins of approx. 19 kDa and approx. 17 kDa (FIG. 1B, Lane 2). The smaller of the two proteins tends to be produced in greater amounts than does the approx. 19 kDa protein. Depending upon the culture conditions, the approx. 19 kDa protein may be present in equivalent amounts to the approx. 17 kDa protein or noticeably less. This may explain why the approx. 17 kDa protein is often observed as being a stronger immunopositive band than the approx. 19 kDa when visualised by Western blotting. Family C has 10 members characterised by a small protein of approx. 13 kDa in size (FIG. 1B, Lane 3) which is often more easily distinguished on Western blot than on CBB stained gel. Clonal variation in expression levels of the protein exist and the signal on blots can vary from weak to strong. Family E is represented by one clone that encodes a protein of approx. 36 kDa (FIG. 2, Lane 2). Family F is also represented by one clone which expresses an abundant amount of an approx. 55 kDa protein (FIG. 1B, Lane 5). Of all the cloned proteins, this protein is the most strongly recognised by the anti-H. felis mouse sera when observed on a Western blot. Family G has 2 members that express an approx. 50 kDa protein (FIG. 1B, lane 6) which is not produced in a quantity that can be easily visualised on a CBB stained gel over and above the equivalent sized host E.coli protein (FIG. 1A, lane 6). However, antibodies in the mouse sera clearly demonstrate binding to this protein and not to the E.coli proteins run in lane 8. Given that this cloned H.pylori protein is not expressed in high amounts but is quite immunopositive, it may well be an important antigen in eliciting a strong immune response to Helicobacter pylori infection. Lane 7 (FIGS. 1A and 1B) contains the only representative of family H, an approx. 29 kDa protein which is poorly expressed and gives a weaker signal than other family proteins on a Western blot. Lane 8 FIG. 1 and Lane 4, FIG. 2 comprises the negative control, E.coli XLOLR bearing expression plasmid pBK-CMV without H.pylori insert. Absorption of the mouse sera with E.coli extract largely prevented non-specific binding to host cell proteins. Depending upon the length of development time of the substrate a maximum of six E.coli proteins were recognised throughout all the lanes compared with a plethora of host cell proteins appearing on blots probed with unabsorbed mouse sera (data not shown). A dominant host cell protein is recognised at 37 kDa. Lane 9 comprises the positive control, total cell proteins of Helicobacter pylori with~10 immunopositive bands ranging in size from 11 to 95 kDa. Results of the sibling DNA analysis (data not shown) confirmed the Western blot data that seven families of cloned H.pylori proteins exist.

The clones were screened for the presence of urease since the genomic DNA used in the generation of the library was obtained from a Ure B positive strain of H.pylori, and urease is a known protective antigen which already has been cloned (Michetti et al, 1994). Hybridization with oligonucleotide probes to Ure A and Ure B genes revealed five clones to be positive for both urease A and urease B DNA sequences (Table 1). All the urease positive clones belong to family A. No other clones existing outside of family A were urease positive. Identity of the approx. 62 kDa and approx. 33 kDa proteins was confirmed by N-terminal sequencing. Protein homology searches in the database Swiss-Prot/GenPeptide identified 100% homology of the 15 amino acid residues of the approx. 62 kDa protein with the Urease B subunit of Helicobacter pylori. The 18 amino acid sequence of the approx. 33 kDa protein was found to have 94.4% homology with the Urease A subunit, with only one mismatched amino acid residue.

Preliminary N-terminal sequence has also been obtained for family B, family C, family F and family G. The protein sequence of the approx. 19 kDa protein of family B has been found to correspond to the membrane-associated lipoprotein antigen (Lpp20) of Helicobacter pylori (Kostrzynska et al., 1994).

No significant homology was found in the data base to the approx. 13 kDa protein of family C or the approx. 36 kDa protein of family E.

Protein sequence data for the 55 kDa protein from family F was found to have 80% homology with the first 15 N-terminal amino acids of the heat shock protein 60 (Hsp60) sequence of *Helicobacter pylori*, with only three residues unmatched. This finding supports the Western blotting results and explains the high signal intensity of this immunoreactive band, as Hsp60 is known to elicit a strong antibody response.

4. Deletion clones were size-selected for DNA sequencing by electrophoresis on agarose gels.

5. DNA sequencing was performed using standard dideoxynucleotide termination reactions containing 7-deaza dGTP. 7-deaza dITP was used, if necessary, to resolve severe GC band compressions. [$^{35}$S]dATP or [$^{33}$P]dATP were used as the label.

TABLE 1

Summary of cloned *H. pylori* antigen families.
N-terminal sequences were compared with those in the Swiss-Prot/GenPeptide database.

| Family | No. of Clones | Urease Hybridization Oligo A & B | Protein Molecular Mass (kDa) | Protein N-terminal Sequence | SEQ ID NO. | Protein Identity (from database) |
| --- | --- | --- | --- | --- | --- | --- |
| A | 5 | Yes | ~62 | MKKISRKEYV | 11 | Urease B sub-unit |
|   |   |   | ~33 | MKLTPKELDKLMLHRAGE | 12 | Urease A sub-unit |
| B | 14 | No | ~19 | MLNQVLLKLGMSVKAAMV | 13 | Lpp20 |
|   |   |   | ~17 | Not determined |   | Mature Lpp20 |
| C | 10 | No | ~13 | MISKEEVLEYIGSLS | 14 | Unknown |
| E | 1 | No | ~36 | Not determined |   | Unknown |
| F | 1 | No | ~55 | AKEIKFVDAARNLFF | 15 | Hsp 60 |
| G | 2 | No | ~50 | MFGFKQLQLQFSQKV | 16 | Unknown |
| H | 1 | No | ~29 | Not determined |   | Unknown |

Subsequently, DNA sequencing has identified some errors in the N-terminal amino acid sequences determined above.

EXAMPLE 2

Selected representative clones from cloned *H. pylori* antigen families C, E, G, H and B (Table 1) have been sequenced as follows:

(i) Clone C.3.5 (SEQ ID NO. 1 and 2)

The strategy used to sequence the 4423 bp insert in clone C3.5 included a combination of procedures which are summarized below.

1. Plasmid DNA was prepared using a modified alkaline lysis procedure.

2. Nested deletions were generated from both the T7 and T3 ends using ExoIII and S1 nuclease.

3. Deletion clones were size-selected for DNA sequencing by electrophoresis on agarose gels.

4. DNA sequencing was performed using standard dideoxynucleotide termination reactions containing 7-deaza dGTP. 7-deaza dITP was used, if necessary, to resolve severe GC band compressions. [$^{35}$S]dATP was used as the label.

5. Sequencing reactions were analysed on 6% polyacrylamide wedge gels containing 8M urea. All samples were loaded in the order G-A-T-C.

6. Internal sequencing primers were synthesised as necessary.

(ii) Clone E2.5 (SEQ ID NO. 3 and 4)

The strategy used to sequence the 2435 bp insert in clone E2.5 included a combination of procedures which are summarised below.

1. The NotI/SalI fragment was blunt-ended, cloned into the EcoRV site of pBluescript II SK$^+$ (Stratagene) and used to transform XL1-Blue cells.

2. Plasmid DNA was prepared using a modified alkaline lysis procedure. The deletion clones were generated from both the original clone and the EcoRV subclone.

3. Plasmid DNA was prepared using a modified alkaline lysis procedure.

4. Deletion clones were size-selected for DNA sequencing by electrophoresis on agarose gels.

5. DNA sequencing was performed using standard dideoxynucleotide termination reactions containing 7-deaza dGTP. 7-deaza dITP was used, if necessary, to resolve severe GC band compressions. [$^{35}$S]dATP or [$^{33}$P]dATP were used as the label.

6. Sequencing reactions were analysed on 6% polyacrylamide wedge gels containing 8M urea. All samples were loaded in the order G-A-T-C.

7. Internal sequencing primers were synthesised as necessary.

(iii) Clone G3.8 (SEQ ID No. 5 and 6)

The strategy used to sequence the 6081 bp BamHI insert in clone G3.8 included a combination of procedures which are summarised below.

1. Nested deletions were generated from both the T7 and T3 ends using ExoIII and S1 nuclease.

2. Plasmid DNA was prepared using a modified alkaline lysis procedure.

3. Deletion clones were size-selected for DNA sequencing by electrophoresis on agarose gels.

4. DNA sequencing was performed using standard dideoxynucleotide termination reactions containing 7-deaza dGTP. 7-deaza dITP was used, if necessary, to resolve severe GC band compressions. [$^{35}$S]dATP was used as the label.

5. Sequencing reactions were analysed on 6% polyacrylamide wedge gels containing 8M urea. All samples were loaded in the order G-A-T-C.

6. Internal sequencing primers were synthesized as necessary.

(iv) Clone H5.1 (SEQ ID NO. 7 and 8)

The strategy used to sequence the 1199 bp insert in clone H5.1 included a combination of procedures which are summarised below.

1. The SalI/NotI fragment was blunt-ended and cloned into the EcoRV site of pBluescript II SK$^+$ (Stratagene) and used to transform XL1-Blue cells.

2. Nested deletions were generated from both the T7 and T3 ends using ExoIII and S1 nuclease.

3. Plasmid DNA was prepared using a modified alkaline lysis procedure.

4. Deletion clones were size-selected for DNA sequencing by electrophoresis on agarose gels.

5. DNA sequencing was performed using standard dideoxynucleotide termination reactions containing 7-deaza dGTP. 7-deaza dITP was used, if necessary, to resolve severe GC band compressions. [$^{35}$S]dATP was used as the label.

6. Sequencing reactions were analysed on 6% polyacrylamide wedge gels containing 8M urea. All samples were loaded in the order G-A-T-C.

7. Internal sequencing primers were synthesised as necessary.

(v) Clone B4.6 (SEQ ID NO. 9 and 10)

The strategy used to sequence the 4518 bp insert in clone B4.6 included a combination of procedures which are summarised below:

1. Plasmid DNA was prepared using a modified alkaline lysis procedure.

2. Nested deletions were generated from both the T7 and T3 ends using Exo III and S1 nuclease.

3. Deleted clones were size-elected for DNA sequencing by electrophoresis on agarose gels.

4. DNA sequencing was performed using standard dideoxynucleotide termination reactions containing 7-deaza dGTP. 7-deaza dIPT was used, if necessary, to resolve severe GC band compressions. [$^{35}$S]dATP was used as the label.

5. Sequencing reactions were analysed on 6% polyacrylamide wedge gels containing 8M urea. All samples were loaded in the order G-A-T-C.

6. Internal sequencing primers were synthesized as necessary.

EXAMPLE 3

Subcloning, Expression, Purification, and Testing of Recombinant *H. pylori* Antigens in an *H. pylori* Mouse Model 1. Development of the *H. pylori* Mouse Model 1.1 Introduction A human strain of *H.pylori* has been adapted to survive in the mouse gastric mucosa thus producing a useful model of *H.pylori* infection. This model was used for these vaccine studies. Detailed below is the method of derivation of this strain, characteristics of the mouse model and the methods used to demonstrate the effectiveness of the recombinant antigens of the present invention.

1.2 Mouse adaptation

A number of biopsies and fresh clinical isolates of *H. pylori* were obtained from patients. Homogenised biopsies and/or fresh clinical isolates were inoculated per os into specific pathogen free (SPF) BALB/c mice. Gastric samples from the infected mice were examined by direct phase microscopy and urease assay. One group of animals, inoculated with a mixture of four clinical isolates, were found to be colonised with spiral-shaped bacteria which gave a positive urease result. Gastric mucus from the colonised animals was cultured on blood agar base containing 5% horse blood and vancomycin (100 μg/ml), polymyxin B (3.3 μg/ml), bacitracin (200 μg/ml), nalidixic acid (10.7 μg/ml) and amphotericin B (50 μg/ml). Representative colonies were examined by phase contrast microscopy and urease and catalase activity was determined. DNA was extracted from those colonies found to have characteristics of *H. pylori* i.e. spiral-shaped, urease and catalase positive. Isolates were confirmed as belonging to the Helicobacter genus by a Helicobacter specific PCR. To identify which of the four clinical isolates had colonised the mice, RAPD's were performed. Resulting finger prints from the original human clinical isolates and the mouse isolates were compared. The results of this comparison showed that all mice had been colonised with only one of the four clinical isolates originally inoculated into the mice. The human and mouse isolates were also found to be vacA and cagA positive by PCR. The mouse isolates were subsequently passaged through mice an additional three times.

One of the isolates, designated HpM8, obtained from a SJL mouse colonised with the original culture and a homogenate from an infected mouse was selected as our standard mouse adapted culture. This isolate has been called the "Sydney Strain" of *H.pylori* (The strain has been redesignated Syd1 and has been deposited in the culture collection of the School of Microbiology & Immunology at The University of New South Wales. (World Directory of Collections of Cultures of Microorganisms. Registration Number 248).

1.3 Mouse strain specificity

Isolate Syd1 was found to colonise a number of strains of mice including BALB/c, DBA, SJL, C3H/He, C3H/HeJ, C57BL/6 and Quackenbush/Swiss. The bacteria were found to colonise all regions of the mouse stomach i.e. the antrum, body and cardia equivalent region, with the bacteria preferentially colonising the border region between the antrum and body mucosa in some strains of mice. The colonisation pattern was found to vary depending upon the strain of mouse inoculated. BALB/c mice were selected for the present study. Electron microscopy revealed a close association of the bacteria with the epithelial surface, occasionally forming adhesion pedestals as seen with human infections. For routine assay of colonisation, urease reactivity was shown to correlate well with bacterial count and so was used as the assay method for *H. pylori* colonisation.

2. Subcloning Antigen Coding Regions into *E.coli* Expression Vectors

The specific antigen coding sequences from *H.pylori* cloned families B,C,E,G and H were isolated by PCR amplification of representative clones using oligonucleotides designed to contain appropriate restriction endonuclease sites to enable cloning into particular expression vectors (Table 2).

Amplified products from families B,C and E were cloned into the XmaI/BglII sites of pGEX-STOP vector (a modified version of pGEX-4T-1 (Pharmacia) in which a termination codon has been inserted close to the N-terminus of GST and a ribosome-binding site, extra restriction sites and a six-histidine tag inserted within the multiple cloning site). This allowed the production of a non-fusion protein containing a C-terminal hexa-histidine tag (hexa-HIS). Constructs of families C and B were expressed in *E.coli* strain ER1793, while family E was expressed in *E.coli* BL21.

The amplified product from family G was cloned into the NcoI/EcoRI sites of pSE420 (Invitrogen) and expressed in *E.coli* strain JM109 to provide a non-fusion protein which did not contain a purification tag.

In the case of family H, where the production of a native protein proved to be a difficult task, the amplified product was cloned into the BamHI/EcoRI sites of pGEX-3X to produce a GST fusion protein in *E.coli* strain JM109

TABLE 2

OLIGONUCLEOTIDES USED FOR PCR

| Family | Forward | Reverse |
|---|---|---|
| B | 5'CGCCCGGGATGAAAAATCAAGTT AAAAAAATT3' (SEQ ID NO. 17) | 5'GCAGATCTAACCTACTTTT AACCATGCCCAA3' (SEQ ID NO. 18) |
| C | 5'GGGCCCGGGATGGCAATTTCAAA AGAAG3' (SEQ ID NO. 19) | 5'GGGGTCGACTAAGATCTCTTGACTT CAACCTTAGCG3' (SEQ ID NO. 20) |
| E | 5'GCGCCCCGGGATGTCAAATAGCA TGTTGGATAAAAATAAA3' (SEQ ID NO. 21) | 5'GCGCAGATCTAGGTTTAATGGTAAC TAACACGCTCATCCG3' (SEQ ID NO. 22) |
| G | 5'CATGCCATGGGCTTTGGGAATAA GCAGTTGCAAC3' (SEQ ID NO. 23) | 5'CGGAATTCTCATTCGCCTTTTTGAATT TTTCAATG3' (SEQ ID NO. 24) |
| H | 5'CATGCCATGGGATACGCAAGCAA ATTAGCC3' (SEQ ID NO. 25) | 5'CGGAATTCTTATCGGCTTGAAGTGTT CTTTTTC3' (SEQ ID NO. 26) |

3. Growth Conditions and the Production of Recombinant Protein

These recombinant clones were grown at 37° C. in Terrific broth (Tartof and Hobbs (1987) and the induction of recombinant protein production was achieved by the addition of IPTG to a final concentration of 1 mM, with continued incubation overnight. Cells were harvested and stored frozen, either for subsequent protein purification or for sonication and use as a whole-cell immunogen.

4. Purification of Recombinant Proteins 4.1 Isolation and Purification of *Helicobacter pylori* Recombinant Protein B 4.1.1 Introduction Protein B was expressed with a Hexa-HIS tag to enable Immobilised Metal Affinity Chromatography (IMAC) to be used in the purification process.

4.1.2 Isolation of Protein B from *E. coli* cell pellets

A cell pellet was obtained from a culture (approximately 32 L) of *E. coli* cells expressing Protein B. The pellet was added to 520 ml of 50 mM phosphate/50 mM NaCl/1 mM EDTA/5%(v/v) glycerol/0.05%NaN$_3$, pH 7.5 and resuspended by gentle stirring. The suspension was subjected to sonication on ice for a total of 3 min, at an amplitude of 15 μm, with a pause of 1 min following each minute of sonication. Complete cell lysis was confirmed by light microscopy.

The sonicated suspension was centrifuged for 30 min at 3200×g in a JA-10 rotor (Beckman, USA). Most of the supernatant was decanted, the pellet resuspended in 400 ml of Phosphate/NaCl buffer (50 mM phosphate/0.5 M NaCl/0.05%NaN$_3$, pH 7.5) and centrifuged at 5000×g. The resulting pellet was resuspended in Phosphate/NaCl buffer containing 0.1% Tween, centrifuged and the pellet finally solubilized in Phosphate/NaCl buffer containing 7.5M urea by agitation on ice overnight. The preparation was then centrifuged at 10000×g, supernatant collected and centrifuged twice more and the resulting supernatant (690 ml) was collected. An additional amount of Protein B was also prepared from *E. coli* cell pellets derived from a further 32L of culture.

4.1.3 Partial purification of Protein B by Immobilised Metal Affinity Chromatography (IMAC)

Each final preparation of Protein B described, was applied to a column (flow rate, 2 ml/min) of Chelating Sepharose Fast Flow (50 mm×100 mm or 26 mm×104 mm, Pharmacia, Sweden) that had been charged with Nickel according to the manufacturers instructions. Contaminants binding to the column were eluted by washing the column with 10 column volumes of 20 mM phosphate/0.5M NaCl/ 0.05M Imidazole/7.5M urea, pH 7.5. Protein B was eluted from the column using 20 mM phosphate/50 mM NaCl/7.5M urea, pH 6.0 at a flow rate of 3 ml/min. Fractions were collected and peaks eluting from the column were monitored by absorbance at 280 nm. Fractions were examined by SDS-PAGE and Western transfer using rabbit serum raised against *Helicobacter pylori*.

4.1.4 Refolding and Further Purification of Protein B

In order to refold and remove urea from partially-purified protein B, fractions eluted from the IMAC column containing Protein B were pooled and dialyzed against 20 mM phosphate/500 mM NaCl, pH 7.5 (5L) with one change of buffer, then dialyzed against 20 mM phosphate/50 mM NaCl, pH 7.5. The retentate was centrifuged at 3000×g in a GPR centrifuge (Beckman) for 30 min, the supernatant collected and set aside for further purification. The pellet was resuspended in 20 mM phosphate/50 mM NaCl, pH 7.5 containing 7.5M urea then dialyzed against a tenfold volume of 0.8M arginine to help in protein refolding and partially remove urea. Protein content in the resulting retentate was estimated by the DC Protein assay (BioRad, USA) according to the manufacturer's instructions using Bovine Serum Albumin as standard. Fractions were analysed for purity by SDS-PAGE and by scanning of separated samples using a Densitometer (Molecular Dynamics). Finally, sucrose was added to the retentate to a final concentration of 10% (w/v) and aliquots were stored at −20° C.

4.1.5 Further Purification of B Soluble Fraction

The soluble fraction of Protein B prepared above was further purified by passage through an IMAC column (16 mm×136 mm) as in 4.1.3, using buffers containing no urea. Protein B was eluted from the IMAC column using a linear gradient of 20 mM phosphate/150 mM NaCl, pH 7.5 containing 0–100% 0.5M Imidazole for 45 min at a flow rate of 3 ml/min. Fractions containing protein B were pooled and dialyzed exhaustively against PBS. The retentate was finally assessed for purity and protein content and sucrose was added to the preparation as described above. Aliquots of the preparation were stored at −20° C.

4.2 Isolation and Purification of *Helicobacter pylori* Recombinant Protein C 4.2.1 Introduction Protein C protein was expressed with a Hexa-HIS tag to enable Immobilised Metal Affinity Chromatography (IMAC) to be used in the purification process.

4.2.2 Isolation of Protein C from *E. coli* Cell Pellets

A cell pellet was obtained from a culture (approximately 56 L) of *E. coli* cells expressing Protein C. A volume (900 ml) of 50 mM phosphate/50 mM NaCl/1 mM EDTA/5%(v/v) glycerol/0.05%NaN$_3$, pH 7.5 was added to the cell pellet and the pellet was resuspended by gentle stirring. The suspension was subjected to sonication on ice for a total of 3 min at an amplitude of 16 μm, with a pause of 1 min following each minute of sonication. Complete cell lysis was confirmed by light microscopy.

The sonicated suspension was centrifuged for 30 min at 5000×g in a JA-10 rotor (Beckman, USA). Supernatant was collected and further clarified by centrifugation at 16000×g. Most of the resulting supernatant (1025 ml) was collected while 55 ml of partially clarified supernatant was filtered by passage through a 0.45 μm membrane (Millipore, USA) and set aside. The supernatant was centrifuged twice more such that virtually no pellet was evident. The final supernatant (825 ml) was combined with filtrate (45 ml) for application to an immobilised metal affinity chromatography column.

4.2.3 Purification of Protein C by Immobilised Metal Affinity Chromatography (IMAC)

The preparation of Protein C described above was applied to a column (flow rate, 3 ml/min) of Chelating Sepharose Fast Flow (50 mm×100 mm, Pharmacia, Sweden) that had been charged with Nickel according to the manufacturer's instructions. Contaminants binding to the column were eluted by washing the column with 10 column volumes of 20 mM phosphate/0.5M NaCl/0.05M Imidazole, pH 7.5. Protein C was eluted from the column using a linear gradient of 20 mM phosphate/50 mM NaCl, pH 7.5 containing 0–100% 0.5M Imidazole for 100 min at a flow rate of 10 ml/min. Fractions (15 ml) were collected and peaks eluting from the column were monitored by absorbance at 280 nm. Fractions were examined by SDS-PAGE and Western transfer using mouse serum raised against *Helicobacter felis*.

4.3 Isolation and Purification of *Helicobacter pylori* Recombinant Protein E

4.3.1 Sonication

*E. coli* cells expressing protein E were pelleted, and resuspended in phosphate buffered saline (PBS; 7.7 mM Na$_2$HPO$_4$, 150 mM NaCl, 2.25 mM NaH$_2$PO$_4$). The cells were placed on ice, and sonicated for 3 min (3×1 min bursts with 1 min intervals) with a sonic cell disrupter. Complete cell destruction was ascertained by phase contrast microscopy. The sonicates were then centrifuged at 10 000 g for 20 min, and the pellets retained. The pellets were then washed with PBS and the centrifugation was repeated.

Sonicate pellets were solubilised in 25 mM Tris, 7M urea, pH 9.5 for 2 hrs at room temperature. Any remaining particulates were removed by 3 centrifugations at 25000 g for 30 minutes. The resulting supernatant was retained for chromatography.

4.3.2 Chromatography

A 60×100 mm Q Sepharose High Performance (anion exchange) column (Pharmacia) was equilibrated at 85 cm/hr (40 ml/min) with 3 column volumes of 25 mM Tris, 7M Urea, pH 9.5. Solubilised material was injected onto the column and washed through with 3 column volumes of the same buffer. The unbound material together with the first two column volumes of wash were collected. Bound material was then removed from the column with a further 3 column volumes of 25 mM Tris, 7M Urea, 1M NaCl, pH 9.5.

The unbound material from chromatography was concentrated in a stirred cell under nitrogen, using a YM 10 (10 kDa cutoff) membrane. The concentrate (25 ml) was then dialysed against 50 mM Tris, 2M urea, pH 8 (5L), for 36 hours at 4° C., to lower the urea concentration of the sample.

4.4 Isolation and Purification of *Helicobacter pylori* Recombinant Protein G

*E. coli* cells expressing Protein G were received for purification as a cell pellet. The cells were suspended in approximately two volumes of 50 mM Tris-HCl, 5% glycerol, 1 mM dithiothreitol, 1 mM Pefabloc SC (Boehringer Mannheim, Germany) and lysed on ice by sonication (MSE). The lysate was centrifuged at 3000 g for 30 minutes. The supernatant was removed and centrifuged at 10,000 g for 30 minutes.

After adjusting the pH to 8.0 and the conductivity to <5.5 mS, the supernatant was applied to a Hiload Q Sepharose HP XK 26/10 (Pharmacia) column. Bound protein was eluted with a linear gradient 0–1M NaCl in 50 mM Tris-HCl pH 8.0. A peak which eluted at 0.2M NaCl was identified by SDS-PAGE to contain Protein G. Fractions from this peak were pooled.

Protein concentration was estimated using the BioRad (U.S.A.) protein assay and a bovine serum albumin standard.

4.5 Isolation and Purification of *Helicobacter pylori* Recombinant Protein H

4.5.1 Process Summary

Briefly the process consists of sonication of *E. coli* cells, solubilization of impurities in detergent, centrifugation, re-sonication of the centrifugation pellet, solubilization of impurities in detergent, centrifugation, solubilization of the centrifugation pellet in 7M urea, filtration, capture of impurities on an anion exchange column, concentration of column non-adsorbed on an ultrafiltration membrane, adjustment of the pH to 9.5, capture of impurities on an anion exchange column, concentration of column non-adsorbed on an ultrafiltration membrane, and partial dilution.

Protein concentrations were determined by Bradford dye binding assay for total protein. All steps were performed at ambient temperatures unless noted.

4.5.2 *E. coli* Cell Disruption by Sonication

The cells were stored at −70° C. The frozen cells were thawed in a 37° C. water bath and suspended into 50 μL of the sonication buffer (10 mM phosphate +150 mM NaCl pH 7.2) per mL of culture. The *E. coli* cells were broken apart by the sonication in 35 mL lots at an amplitude of~10μ for one minute followed by one minute rest, three times. The samples were bathed in ice water while being sonicated. The pre and post sonicated cells were stored in crushed ice during the sonication process.

4.5.3 Solubilization of Impurities in Detergent

Detergent Triton X100 20% v/v was added to the sonicated *E. coli* cell preparation slowly while stirring to a final Triton X100 concentration of 1% v/v. This was stirred gently with a magnetic flea for 30 minutes.

4.5.4 Centrifugation

The triton X100 treated sonicate was next centrifuged at a RCF of 34,000 g for 30 minutes and the resulting pellet stored at −20%C over night.

4.5.5 Re-sonication of the centrifugation pellet

The centrifugation pellet was re-suspended by adding it to 3 times its volume of sonication buffer (10 mM phosphate +150 mM NaCl pH 7.2) and vigorously agitating for~2 minutes. This was sonicated as before.

4.5.6 Solubilization of Impurities in Detergent

Detergent Triton X100 20% v/v was added to the re-sonicated centrifugation pellet preparation slowly while stirring to a final Triton X100 concentration of 1% v/v. This was stirred gently with a magnetic flea for 30 minutes.

4.5.7 Centrifugation

The Triton X100 treated sonicate was centrifuged at a RCF of 34,000 g for 30 minutes.

4.5.8 Solubilization in Urea

The centrifuge pellet of the detergent treated re-sonicate was solubilized by added 100 mL 20 mM Tris (hydroxymethyl)methylamine +7.5M urea pH 8.0 per 500 mL of cell culture and this was stirred with a magnetic flea for 10 minutes.

4.5.9 Filtration

The solubilized centrifuge pellet was filtered through a series of filters. First Millipore pre-filter AW followed by Millipore filter 0.8 $\mu$m (type AA) and finally Millipore filter 0.45 $\mu$m (type HVLP).

4.5.10 Capture of Impurities by Anion Exchange Chromatography 60 mL of the filtered preparation was loaded onto a Pharmacia Q Sepharose HP column (dimensions 2.6×10.9 cm). The column had been equilibrated with 3 column volumes of 30 mM Tris(hydroxymethyl)methylamine +7.5M urea pH 8.0 (Buffer A). The sample was loaded on to the column at 50 cm/hr and the column washed after loading with buffer A at 120 cm/hr. The non-adsorbed fraction off the column contained the antigen while much of the contaminating material bound to the column.

4.5.11 Concentration

The non-adsorbed fraction was concentrated 10 fold using an AMICON YM30 30 kDa cut off ultrafiltration membrane.

4.5.12 Capture of Impurities by Anion Exchange Chromatography

The pH of all of the concentrated non-adsorbed fraction was adjusted from 8.0 to 9.5 with 1M NaOH. This was loaded onto a Pharmacia Q Sepharose HP column (dimensions 2.6×10.9 cm). The column had been equilibrated with 3 column volumes of 30 mM Tris (hydroxymethyl)methylamine +7.0M urea pH 9.5 (Buffer A). The sample was loaded onto the column and then washed with Buffer A at 56 cm/hr. The non-adsorbed fraction off the column contained the antigen while much of the contaminating material bound to the column.

4.5.13 Concentration and Dilution

The non-adsorbed material was concentrated~10 fold using an AMICON YM30 30 kDa cut off ultrafiltration membrane. The concentration of urea was reduced by dilution of the final product with 10 mM phosphate +150 mM NaCl pH 7.2.

5. Immunisation Protocol 5.1 Method

Female SPF BALB/c mice aged 6–8 weeks were selected for the experiment. Mice were immunised ora-gastrically with up to 200 $\mu$g of protein plus 10 $\mu$g cholera toxin (Sigma).

Test groups included single purified recombinant protein antigens, and also a combination of some proteins. Also tested were preparations of sonicated *E. coli* cells expressing recombinant antigens, which had not undergone a purification process. A combination of these sonicates was also tested. A positive control group of *H. pylori* sonicate +CT was included. Also, negative control groups were immunised with CT alone, or PBS alone, (both challenged) and unimmunised, unchallenged animals. A representative portion of mice were bled from the tail vein prior to challenge.

Mice were challenged with 3 doses of *H. pylori*, starting 1 week after immunisation. Three weeks after *H. pylori* challenge mice were euthanased and stomachs, sera, saliva & bile collected for assessment of infection and immune responses.

5.2 Dosage Rates

Mice were dosed with volumes according to the schedule below.

100 $\mu$l/dose/mouse (a) HPCT: 1 mg of whole cell *H. pylori* sonicate +10 $\mu$g CT (b) CT Alone: 10 $\mu$g CT in PBS (c) Purified C: 200 $\mu$g of protein +10 $\mu$g CT (d) Sonicates of B, C, E, G, H: +10 $\mu$g CT 150 $\mu$l/dose/mouse (e) Purified G: 200 $\mu$g of protein +10 $\mu$g CT 250 $\mu$l/dose/mouse (f) Purified B: ~114 $\mu$g of protein +10 $\mu$g CT (g) Purified E: 50 $\mu$g of protein +10 $\mu$g CT (h) Combination A: equal amount of purified protein B, C & G +1 $\mu$g CT (i) Combination B: equal amount of sonicates from B, C, E, G & H +10 $\mu$g CT 350 $\mu$l/dose/mouse (j) Purified H: ~50 $\mu$g of protein +10 $\mu$g CT given in 2 doses—one 200 $\mu$l dose, followed by a 150 $\mu$l dose 5.3 Experiment Outline

TABLE 3

| | MOUSE GROUPS | | | | |
|---|---|---|---|---|---|
| DAY | Hp + CT [10] | PBS Alone [10] | CT Alone [10] | Test Ag + CT* [10] | Normal [10] |
| 0 | HpCT | PBS | CT | Ag + CT | Normal |
| 7 | HpCT | PBS | CT | Ag + CT | Normal |
| 14 | HpCT | PBS | CT | Ag + CT | Normal |
| 21 | HpCT | PBS | CT | Ag + CT | Normal |
| 28 | Pre-challenge Bleed | | | | |
| 28 | *H. pylori* (10/group) challenge | | | | — |
| 30 | *H. pylori* (10/group) challenge | | | | — |
| 32 | *H. pylori* (10/group) challenge | | | | — |
| 52 & 53 | Collect groups challenged with *H. pylori* | | | | — |

*5 recombinant antigens, each to be administered separately, and in combination with the other recombinant antigens. Antigens tested as purified proteins or whole-cell sonicates.

5.4 Challenge

*H.pylori* Syd 1 was grown up in liquid culture (BHI broth supplemented with 5% horse serum and Skirrow's selective supplement) under microaerophilic conditions for 2 days. The cells were centrifuged at 9000 rpm for 15 mins and the concentration adjusted to approximately $10^9$ cells per ml. Immunised mice and controls were challenged one week post the completion of the vaccine schedule with 0.1 ml of this suspension which was made fresh each day. Urease assay of the animals to detect colonisation was performed 24 days after challenge.

6. Results

TABLE 4

| GROUP | H. pylori infected (+ve urease test) No. infected/total |
|---|---|
| Purified Recombinant Antigens | |
| Protein B | 0/10 |
| Protein C | 1/10 |
| Protein E | 0/9 |
| Protein G | 3/8 |
| Protein H | 1/10 |
| Combination | 1/10 |
| Sonicated E. coli cells expressing recombinant antigens | |
| Protein B expressing cells | 8/10 |
| Protein C expressing cells | 8/10 |
| Protein E expressing cells | 3/9 |
| Protein G expressing cells | 7/10 |
| Protein H expressing cells | 6/10 |
| Combination | 7/10 |
| Controls | |
| H. pylori sonicated cells + CT immunised (+ve control) | 0/10 |
| PBS immunised (−ve control) | 8/9 |
| CT immunised | 9/10 |
| Not immunised, not challenged | 0/10 |

These results show that ora-gastric immunisation with any of the five purified recombinant proteins in conjunction with a mucosal adjuvant protected mice from infection with *H. pylori*. The results of the unpurified *E. coli* whole-cell sonicates suggest that higher levels of expression or purification are required to demonstrate protection. The gene screening strategy, using serum from immune mice (immunised with *H. felis* sonicate), identified two known *H. pylori* protective antigens, urease and heat shock protein, and five other proteins. The results reported here now show that these five are also protective antigens. One of the five antigens is a previously known compound (Kostrzynska et al, 1994), but it was not previously known whether this compound was a protective antigen. As we have shown that protective immunogenic preparations can be used to treat infection, as well as prevent it, it would be expected that these protective antigens could be used to treat, as well as prevent, Helicobacter infection in humans. The validity of the *Helicobacter felis* mouse model, that was used to identify these *Helicobacter pylori* antigens, has been shown by the ability of these antigens to protect mice in a recently developed *H. pylori* mouse model. It would therefore be expected, that these antigens, alone or in combination, would be protective antigens in products used to treat or prevent Helicobacter infections in humans.

REFERENCES:

Chen, M., Lee, A., and Hazell, S. (1992). Immunisation against gastric helicobacter infection in a mouse/Helicobacter felis model. *Lancet* 339:1120–1121.

Cox, J. and Coulter, A. (1992). Advances in Adjuvant Technology and Application. In Animal Parasite Control Utilising Biotechnology. Edited W. K. Yong, CRC Press.

Doidge, C., Gust, I., Lee, A., Buck, F., Hazell, S. and Manne, U. (1994). Therapeutic immunisation against helicobacter infection. *Lancet*. 343:914–915.

Dick-Hegedus, E. and Lee, A. (1991). Use of a mouse model to examine anti-Helicobacter pylori agents. *Scand. J. Gastroenterol*. 26:909–915.

Ferrero, R. L., Thiberge, J-M., Kansau, I., Wuscher, N., Huerre, M. and Labinge, A. (1995). The GroES homolog of *Helicobacter pylori* confers protective immunity against mucosal infection in mice. *Proc. Natl. Acad. Sci. (USA)*. 92:6499–6503.

Holmgren, J., Czerkinsky, C., Lycke, N. and Svennerholm, A-M. (1992). Mucosal Immunity: Implications for Vaccine Development. *Immunobiol*. 184:157–179.

Lee, A., Fox, J. G., Otto, G., and Murphy, J. (1990). A small animal model of human Helicobacter pylori active chronic gastritis. *Gastroenterology* 99:1315–1323.

Kostrzynska, M., O'Toole, P. W., Taylor, D. E. and Trust, T. J. (1994). Molecular characterization of a conserved 20-kilodalton membrane-associated lipoprotein antigen of *Helicobacter pylori*. *J. Bacteriol*. 176:5938–5948.

Majewski, S. L. H., and Goodwin, C. S. (1988) Restriction endonuclease analysis of the genome of Campylobacter pylori with a rapid extraction method: evidence for considerable genomic variation. *J. Inf. Dis.* 157(3):465–471.

McGhee, J. R., Mestecky, J., Dertzbaugh, M. T., Eldridge, J. H., Hirasawa, M. and Kyono, H. (1992). The mucosal immune system: from fundamental concepts to vaccine development. *Vaccine* 10(2):75–88.

Michetti, P., Corth'sy-Theulaz, I., Davin, C., Haas, R., Vaney, A-C., Heitz, M., Bille, J., Kraehenbuhl, J-P., Saraga, E. and Blum, A. L. (1994). Immunization of BALB/c mice against *Helicobacter felis* infection with *Helicobacter pylori* urease. *Gastroenterology* 107:1002–1011.

Sambrook, J., Fritsch, E. F., and Maniatis, T. (1989) Molecular Cloning: A Laboratory Manual, 2nd edn. Cold Spring Harbor, N.Y.: Cold Spring Harbor Laboratory Press.

Tartof, K. D. and Hobbs, C. A. (1987). *Focus* 9:12.

Towbin, H., Staehelin, T., and Gordon, J. (1979) Electrophoretic transfer of proteins from polyacrylamide gels to nitrocellulose sheets: procedure and some applications. *Proc. Natl. Acad. Sci. (USA)* 74:4350–4354.

What is claimed is:

1. An isolated nucleic acid molecule which encodes a Helicobacter antigen having a molecular mass of approximately 36 kDa, said nucleic acid molecule consisting essentially of the sequence of nucleotides of SEQ ID NO:3.

2. A recombinant DNA molecule comprising an expression control sequence operatively linked to the nucleic acid molecule according to claim 1.

3. The recombinant DNA molecule according to claim 2, wherein said expression control sequence comprises a promoter sequence and an initiator sequence, and said sequence of nucleotides is located 3' to the promoter and initiator sequences.

4. A recombinant DNA cloning vector comprising the recombinant DNA molecule according to claim 2.

5. The recombinant DNA cloning vector according to claim 4, wherein said vector is a plasmid.

6. The host cell transfected or transformed with the recombinant DNA molecule according to claim 1.

7. A host cell according to claim 6, wherein said host cell is *E. coli*.

8. A preparation for use in the treatment or prevention of Helicobacter infection in a mammalian host, which comprises a vector which is a host cell capable of expressing a Heilcobacter antigen having a molecular mass of approximately 36 kDa, wherein said host cell comprises a heterologous nucleic acid molecule consisting essentially of the sequence of nucleotides which encodes SEQ ID NO:4.

9. A preparation according 8, wherein said vector is a bacterium that colonizes the gastrointestinal tract of the mammalian host.

10. A preparation according to claim 8, wherein said vector is a bacterium selected from the group of Salmonella, Shigella, Yersinia, Vibrio, Escherichia and Bacillus Calmette-Guerin (BCG).

11. An isolated nucleic acid molecule which encodes a Helicobacter antigen having a molecular mass of approximately 36 kDa, said nucleic acid molecule consisting essentially of the sequence of nucleotides which encodes SEQ ID NO:4.

* * * * *